United States Patent
Dinnell et al.

(10) Patent No.: US 7,410,964 B2
(45) Date of Patent: Aug. 12, 2008

(54) CYCLOHEXYL SULPHONES AS GAMMA-SECRETASE INHIBITORS

(75) Inventors: Kevin Dinnell, Much Hadham (GB); Karl Richard Gibson, Canterbury (GB); Timothy Harrison, Great Dunmow (GB); Richard Alexander Jelley, Bishops Stortford (GB); Alan John Nadin, Sawbridgeworth (GB); Paul Joseph Oakley, Bishops Stortford (GB); Andrew Pate Owens, Huntingdon (GB); Duncan Edward Shaw, Bishops Stortford (GB); Brian John Williams, Great Dunmow (GB)

(73) Assignee: Merck Sharp & Dohme Ltd., Hoddesdon Hertfordshire (GB)

( * ) Notice: Subject to any disclaimer, the term of this patent is extended or adjusted under 35 U.S.C. 154(b) by 0 days.

(21) Appl. No.: 10/555,034

(22) PCT Filed: May 7, 2004

(86) PCT No.: PCT/GB2004/001973

§ 371 (c)(1),
(2), (4) Date: Oct. 27, 2005

(87) PCT Pub. No.: WO2004/101538

PCT Pub. Date: Nov. 25, 2004

(65) Prior Publication Data

US 2006/0281737 A1 Dec. 14, 2006

(30) Foreign Application Priority Data

May 16, 2003 (GB) .................................. 0311341.2
Nov. 20, 2003 (GB) .................................. 0327055.0

(51) Int. Cl.
*C07D 285/22* (2006.01)
*A61K 31/5415* (2006.01)

(52) U.S. Cl. ..................................... 514/222.8; 544/11
(58) Field of Classification Search .................. 544/11; 514/222.8

See application file for complete search history.

(56) References Cited

U.S. PATENT DOCUMENTS

2004/0230054 A1  11/2004  Dinnell et al.

FOREIGN PATENT DOCUMENTS

| WO | WO 00/50391  | 8/2000  |
| WO | WO 01/70677  | 9/2001  |
| WO | WO 02/36555  | 5/2002  |
| WO | WO 02/081435 | 10/2002 |
| WO | WO 03/055850 | 7/2003  |

OTHER PUBLICATIONS

International Preliminary Report on Patentability for PCT/GB2004/001973 (Nov. 18, 2005).
Written Opinion of the International Searching Authority for PCT/GB2004/001973 (Sep. 28, 2004).

*Primary Examiner*—Kahsay T Habte
(74) *Attorney, Agent, or Firm*—William Krovatin; Raynard Yuro

(57) ABSTRACT

Compounds of formula I:

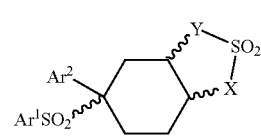

inhibit gamma-secretase and hence find use in treatment or prevention of Alzheimer's disease.

4 Claims, No Drawings

CYCLOHEXYL SULPHONES AS GAMMA-SECRETASE INHIBITORS

CROSS REFERENCE TO RELATED APPLICATIONS

This application is a U.S. National Phase application under 35 U.S.C. § 371 of PCT Application No. PCT/GB2004/001973, filed May 7, 2004, and claims priority under 35 U.S.C. § 119 from GB Application No. 0311341.2, filed May 16, 2003 and GB Application No. 0327055.0, filed Nov. 20, 2003.

The present invention relates to a novel class of compounds, their salts, pharmaceutical compositions comprising them, processes for making them and their use in therapy of the human body. In particular, the invention relates to novel cyclohexyl sulphones comprising an additional fused ring which contains an $SO_2$ group. The compounds inhibit the processing of APP by γ-secretase so as to suppress or attenuate the secretion of β-amyloid, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There is a growing number of reports in the literature of compounds with inhibitory activity towards γ-secretase, as measured in cell-based assays (see, for example, WO 01/70677 and references therein). Many of the relevant compounds are peptides or peptide derivatives.

WO 00/50391 discloses a broad class of sulphonamides as modulators of the production of β-amyloid, but neither discloses nor suggests the compounds of the present invention. WO 01/70677, WO 02/36555 and WO 02/081435 disclose, respectively, classes of sulphonamides, sulphamides and cyclohexyl sulphones which inhibit γ-secretase, but neither disclose nor suggest the compounds of the present invention.

The present invention provides a novel class of cyclohexyl sulphones comprising and additional fused ring which contains an $SO_2$ group. The compounds inhibit the processing of APP by the putative γ-secretase so as to suppress or attenuate the production of Aβ and hence are useful in the treatment or prevention of AD.

According to the invention there is provided a compound of formula I:

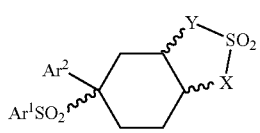

wherein the bonds indicated by wavy lines are mutually cis with respect to the cyclohexane ring;

X represents O, $NR^1$ or $CHR^1$;
Y represents $CHR^2$—$CHR^3$, $CR^2$=$CR^3$, $CHR^2$—$NR^4$ or $CHR^2$—O;
$R^1$ represents H or $C_{1-4}$alkyl;
$R^2$, $R^3$ and $R^4$ independently represent H or a hydrocarbon group of up to 10 carbon atoms, optionally substituted with $CF_3$, $CHF_2$, halogen, CN, $OR^5$, $COR^5$, $CO_2R^5$, $OCOR^6$, $N(R^5)_2$, $CON(R^5)_2$ or $NR^5COR^6$; or $R^2$ and $R^4$ together complete a 5- or 6-membered ring which is optionally substituted with oxo, $CF_3$, $CHF_2$, halogen, CN, $OR^5$, $COR^5$, $CO_2R^5$, $OCOR^6$, $N(R^5)_2$, $CON(R^5)_2$ or $NR^5COR^6$;
$R^5$ represents H or $C_{1-4}$alkyl;
$R^6$ represents $C_{1-4}$alkyl; and
$Ar^1$ and $Ar^2$ independently represent phenyl or heteroaryl, either of which bears 0-3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

or a pharmaceutically acceptable salt thereof.

The compounds of formula I exist in two enantiomeric forms, depending on whether the bonds indicated by wavy lines project upwards or downwards, corresponding to formulae IA and IB:

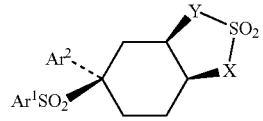

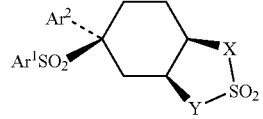

where X, Y, $Ar^1$ and $Ar^2$ have the same meanings as before. It is to be understood that any compound in accordance with the invention may exist in either of the homochiral forms IA and IB, or as a mixture of the two in any proportion.

In addition to the isomerism described above, the compounds according to the invention may comprise one or more asymmetric centres, and accordingly may exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Where a variable occurs more than once in formula I, the individual occurrences are independent of each other, unless otherwise indicated. As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{2-6}$acyl" as used herein refers to $C_{1-5}$alkylcarbonyl groups in which the alkyl portion may be straight chain, branched or cyclic, and may be halogenated. Examples include acetyl, propionyl and trifluoroacetyl.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Monocyclic systems of 5 or 6 members are preferred. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine. Pyridine rings may be in the N-oxide form.

Where a phenyl group or heteroaryl group bears more than one substituent, preferably not more than one of said substituents is other than halogen or alkyl. Where an alkyl group bears more than one substituent, preferably not more than one of said substituents is other than halogen.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, benzenesulfonic acid, methanesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

In the compounds of formula I, $Ar^1$ and $Ar^2$ independently represent optionally substituted phenyl or heteroaryl. $Ar^1$ is preferably selected from optionally substituted phenyl and optionally substituted 6-membered heteroaryl. Preferred 6-membered heteroaryl embodiments of $Ar^1$ include optionally substituted pyridyl, in particular optionally substituted 3-pyridyl. $Ar^1$ is preferably selected from 6-(trifluoromethyl)-3-pyridyl and phenyl which is optionally substituted in the 4-position with halogen, CN, vinyl, allyl, acetyl, methyl or mono-, di- or trifluoromethyl. In one preferred embodiment of the invention $Ar^1$ represents 4-chlorophenyl. In another preferred embodiment $Ar^1$ represents 4-trifluoromethylphenyl.

$Ar^2$ preferably represents optionally substituted phenyl, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5- positions, the 2- and 6-positions or in the 2-, 3- and 6-positions, or from phenyl groups bearing a fluorine substituent in the 2-position and halogen, CN, methyl or hydroxymethyl in the 5-position. In a preferred embodiment of the invention, $Ar^2$ represents 2,5-difluorophenyl, 2,6-difluorophenyl or 2,3,6-trifluorophenyl.

In a particular embodiment, $Ar^1$ is 4-chlorophenyl or 4-trifluoromethylphenyl and $Ar^2$ is 2,5-difluorophenyl.

In formula I, X represents O, $NR^1$ or $CHR^1$. When X represents O, Y is preferably $CHR^2$—$NR^4$ or $CHR^2$—O. When X represents $CHR^1$, Y is preferably $CHR^2$—$CHR^3$, $CR^2$=$CR^3$ or $CHR^2$—$NR^4$, especially $CHR^2$—$CHR^3$ or $CHR^2$—$NR^4$. When Y represents $CR^2$=$CR^3$, X preferably represents $NR^1$.

$R^1$ represents H or $C_{1-4}$alkyl, such as methyl, ethyl, n-propyl or isopropyl, but preferably $R^1$ represents H.

$R^2$ represents H or a hydrocarbon group of up to 10 carbon atoms, optionally substituted as defined previously. Hydrocarbon groups represented by $R^2$ are preferably non-aromatic and unsubstituted, and preferably comprise up to 6 carbon atoms. Typical examples include alkyl groups (such as methyl, ethyl, n-propyl, isopropyl and n-butyl) and alkenyl groups (such as allyl). When Y represents $CHR^2$—$CHR^3$, $CR^2$=$CR^3$ or $CHR^2$—O, $R^2$ very aptly represents H. When Y represents $CHR^2$—$NR^4$, $R^2$ and $R^4$ may combine to form a fused 5- or 6-membered ring, such as a pyrrolidine, piperidine or tetrahydropyridine ring, which is optionally substituted as defined previously. Preferred rings include piperidine and tetrahydropyridine which are unsubstituted or substituted with OH.

$R^3$ represents H or a hydrocarbon group of up to 10 carbon atoms, optionally substituted as defined previously. In one embodiment hydrocarbon groups represented by $R^3$ are non-aromatic and unsubstituted, and preferably comprise up to 6 carbon atoms. Typical examples include alkyl groups (such as methyl, ethyl, n-propyl, isopropyl and n-butyl) and alkenyl groups (such as allyl and 3-methylbut-2-enyl).

In an alternative embodiment, $R^3$ represents $C_{1-6}$alkyl bearing a substituent selected from CN, $OR^5$, $CO_2R^5$, $COR^5$ and $CON(R^5)_2$ where $R^5$ is as defined previously. Preferred substituents include OH, CN, $CO_2H$, $COCH_3$ and $CONH_2$. When Y represents $CR^2$=$CR^3$, $R^3$ very aptly represents H.

$R^4$ represents H or a hydrocarbon group of up to 10 carbon atoms, optionally substituted as defined previously. Preferred substituents include CN, $CF_3$, halogen (especially F), OH and alkoxy (especially methoxy). Suitable hydrocarbon groups include optionally substituted phenyl$C_{1-4}$alkyl (such as benzyl), $C_{1-6}$alkyl, $C_{2-6}$alkenyl, $C_{2-6}$alkynyl, $C_{3-6}$cycloalkyl and $C_{3-6}$cycloalkyl$C_{1-4}$alkyl. Specific examples of groups represented by $R^4$ include H, methyl, ethyl, n-propyl, isopropyl, n-butyl, t-butyl, sec-butyl, 2-fluoroethyl, 2,2,2-trifluoroethyl, 2-cyanoethyl, 2-hydroxyethyl, 2-methoxyethyl, allyl, cyclopropyl, cyclobutyl, cyclopentyl and cyclopropylmethyl. Alternatively, $R^4$ may combine with $R^2$ to form a fused ring as described above.

A subset of the compounds of the invention are those of formula II and the pharmaceutically acceptable salts thereof:

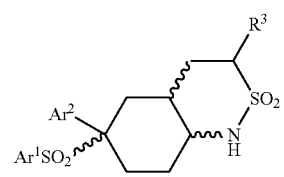

II wherein the bonds indicated by wavy lines are mutually cis with respect to the cyclohexane ring, and R³, Ar¹ and Ar² have the same definitions and preferred identities as before.

Specific examples of compounds within this subset include those in which Ar¹ represents 4-chlorophenyl or 4-trifluoromethylphenyl, Ar² represents 2,5-difluorophenyl, and R³ represents H, methyl, ethyl, n-propyl, isopropyl, allyl, 3-methylbut-2-enyl, cyanomethyl, 2-cyanoethyl, 3-cyanopropyl, 2-hydroxyethyl, —CH₂COCH₃, —CH₂CO₂H, —CH₂CH₂CO₂H, —CH₂CONH₂ or CH₂CH₂CONH₂, and pharmaceutically acceptable salts thereof.

A second subset of the compounds of the invention are those of formula III and the pharmaceutically acceptable salts thereof:

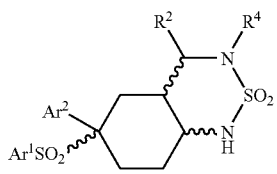

III wherein the bonds indicated by wavy lines are mutually cis with respect to the cyclohexane ring, and R², R⁴, Ar¹ and Ar² have the same definitions and preferred identities as before.

Specific compounds within this subset include those in which Ar² represents 2,5-difluorophenyl and Ar¹, R² and R⁴ are as shown in the following table:

| Ar¹ | R² | R⁴ |
|---|---|---|
| 4-Cl—C₆H₄ | H | ethyl |
| 4-Cl—C₆H₄ | H | n-propyl |
| 4-Cl—C₆H₄ | H | n-butyl |
| 4-Cl—C₆H₄ | H | cyclopropyl |
| 4-Cl—C₆H₄ | H | cyclopentyl |
| 4-Cl—C₆H₄ | H | sec-butyl |
| 4-Cl—C₆H₄ | H | cyclopropylmethyl |
| 4-Cl—C₆H₄ | H | t-butyl |
| 4-Cl—C₆H₄ | H | 2,2,2-trifluoroethyl |
| 4-Cl—C₆H₄ | H | 2-hydroxyethyl |
| 4-Cl—C₆H₄ | H | methyl |
| 4-Cl—C₆H₄ | H | isopropyl |
| 4-Cl—C₆H₄ | H | cyclobutyl |
| 4-Cl—C₆H₄ | H | 2-fluoroethyl |
| 4-CF₃—C₆H₄ | H | ethyl |
| 4-CF₃—C₆H₄ | H | methyl |
| 4-CF₃—C₆H₄ | H | isopropyl |
| 4-CF₃—C₆H₄ | H | cyclopropyl |
| 4-CF₃—C₆H₄ | H | cyclobutyl |
| 4-CF₃—C₆H₄ | H | t-butyl |
| 4-CF₃—C₆H₄ | H | 2,2,2-trifluoroethyl |
| 4-CF₃—C₆H₄ | H | 2-hydroxyethyl |
| 4-CF₃—C₆H₄ | H | 2-fluoroethyl |
| 4-CF₃—C₆H₄ | H | 2-cyanoethyl |
| 4-CF₃—C₆H₄ | H | 2-methoxyethyl |
| 4-Cl—C₆H₄ | allyl | allyl |
| 4-Cl—C₆H₄ | fused tetrahydropyridine | |
| 4-Cl—C₆H₄ | fused piperidine | |
| 4-Cl—C₆H₄ | allyl | isopropyl |
| 4-Cl—C₆H₄ | n-propyl | isopropyl |
| 4-Cl—C₆H₄ | fused 3-hydroxypiperidine | |
| 4-Cl—C₆H₄ | fused 4-hydroxypiperidine | |
| 4-Cl—C₆H₄ | H | H |
| 6-CF₃-pyridin-3-yl | H | cyclopropyl |
| 4-Cl—C₆H₄ | allyl | cyclopropyl |
| 4-Cl—C₆H₄ | 2-hydroxyethyl | cyclopropyl |

| Ar¹ | R² | R⁴ |
|---|---|---|
| 4-Cl—C₆H₄ | H | —CH(CH₃)CH₂OH |
| 4-Cl—C₆H₄ | H | —CH(CH₃)CO₂H |

A third subset of the compounds of the invention are those of formula IV and the pharmaceutically acceptable salts thereof:

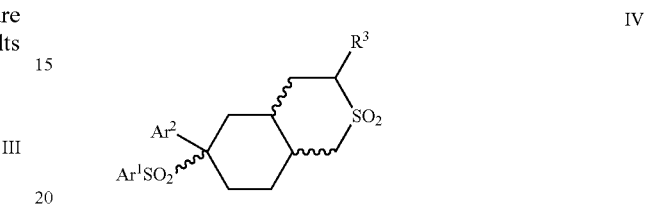

IV wherein the bonds indicate by the wavy lines are mutually cis with respect to the cyclohexane ring, and R³, Ar¹ and Ar² have the same definitions and preferred identities as before.

Specific compounds within this subset include those in which Ar² represents 2,5-difluorophenyl, Ar¹ represents 4-chlorophenyl or 4-trifluoromethylphenyl, and R³ represents H, methyl, ethyl, propyl or cyclobutyl.

Further specific compounds in accordance with the invention are disclosed in the Examples appended hereto.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.05 to 100 mg/kg per day, more preferably about 0.1 to 50 mg/kg of body weight per day, and for the most preferred compounds, about 0.1 to 20 mg/kg of body weight per day. The compounds may be administered on a regimen of 1 to 4 times per day. In some cases, however, a dosage outside these limits may be used.

Compounds of formula I in which Y represents $CHR^2$—$NR^4$ may be prepared by cyclisation of compounds of formula (Ia):

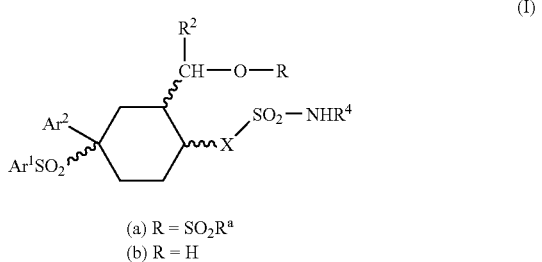

(a) $R = SO_2R^a$
(b) $R = H$ where $R^a$ represents optionally-substituted alkyl or phenyl (especially methyl, tolyl or trifluoromethyl) and $Ar^1$, $Ar^2$, X, $R^2$ and $R^4$ have the same meanings as before. The reaction takes place in the presence of sodium hydride in an aprotic solvent such as THF or DMF at 0-20° C.

Sulphonates (1a) are obtained by treatment of alcohols (1b) with $R^aSO_2Cl$ or $(R^aSO_2)_2O$ in the presence of base under anhydrous conditions, typically at ambient temperature.

Alcohols (1b) in which $R^2$ is H are obtained by cleavage of the silylethyl ethers (2) with $BF_3$ etherate:

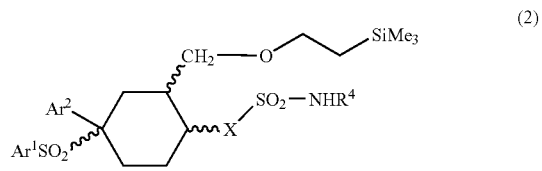

where $Ar^1$, $Ar^2$, X and $R^4$ have the same meanings as before. The reaction may be carried out in dichloromethane at ambient temperature. Secondary alcohols (1b) in which $R^2$ is hydrocarbon may be obtained by oxidation of the corresponding primary alcohols and reaction of the resulting aldehydes with $R^2MgBr$.

Compounds (2) in which X is O are available by reaction of alcohols (3) with $R^4NHSO_2Cl$:

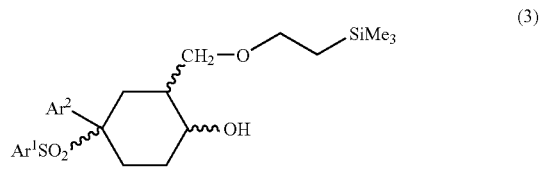

where $Ar^1$, $Ar^2$ and $R^4$ have the same meanings as before. The reaction takes place in dimethylacetamide at 50° C.

Alcohols (3) are obtained by reduction of ketones (4) and isolation of the desired cis isomers:

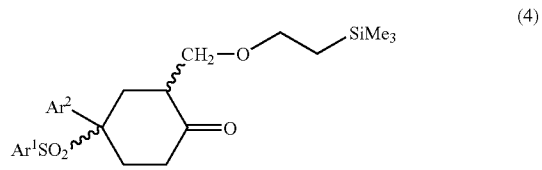

where $Ar^1$ and $Ar^2$, have the same meanings as before. Reduction with L-Selectride™ in THF at −78° C. provides the cis isomers preferentially, while reduction with sodium borohydride in isopropanol at −40 to 20° C. provides roughly equal proportions of the cis and trans isomers which are separable by chromatography.

Ketones (4) are available by alkylation of cyclohexanones (5) with 2-(trimethylsilyl) ethoxymethyl chloride:

where $Ar^1$ and $Ar^2$ have the same meanings as before. The reaction may be carried out in THF at −78° C. in the presence of strong base such as lithium hexamethyldisilazide. As an alternative to lithium hexamethyldisilazide, there may be employed the product obtained from reacting BuLi with a chiral amine such as [S—(R*,R*)]-(−)-bis(α-methylbenzyl)

amine. This enables the isolation of compounds (4) in homochiral form, and hence the synthesis of homochiral compounds of formula I. The preparation of cyclohexanones (5) is described in WO 02/081435 and WO 04/013090.

Compounds (2) in which X is NR$^1$ are obtainable by reaction of amines (6) with R$^4$NHSO$_2$Cl:

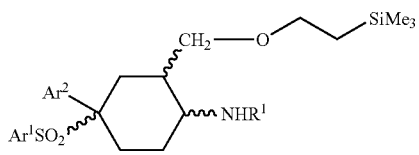

(6)

where Ar$^1$, Ar$^2$, R$^1$ and R$^4$ have the same meanings as before. The reaction may be carried out in the presence of triethylamine in a mixture of dichloromethane and dimethylacetamide at ambient temperature.

Amines (6) may be obtained by treatment of the trans isomers of alcohols (3) with R$^a$SO$_2$Cl or (R$^a$SO$_2$)$_2$O in the presence of base under anhydrous conditions, followed by displacement of the resulting sulphonate esters with R$^1$NH$_2$, where R$^a$ and R$^1$ have the same meanings as before. Alternatively, the sulphonate esters may be displaced using azide ion, and the product reduced to provide amines (6) in which R$^1$ is H. The displacement may be carried out in DMF at 95° C., and the reduction may be effected using triphenylphosphine in refluxing THF.

Compounds (2) in which X is CHR$^1$ may be obtained by reduction of compounds (7), using sodium borohydride and NiCl$_2$ in methanol at 0° C.:

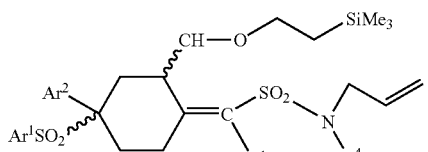

(7)

where Ar$^1$, Ar$^2$, R$^1$ and R$^4$ have the same meanings as before.

Compounds (7) are obtained via condensation of ketones (4) with:

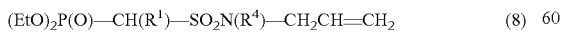

(EtO)$_2$P(O)—CH(R$^1$)—SO$_2$N(R$^4$)—CH$_2$CH=CH$_2$  (8)

where R$^1$ and R$^4$ have the same meanings as before. The reaction may be carried out in THF at −78° C. in the presence of BuLi. Compounds (8) are available by reaction of sulphonamides R$^1$—CH$_2$—SO$_2$N(R$^4$)—CH$_2$CH=CH$_2$ with diethylchlorophosphonate in the presence of BuLi in THF at −78° C.

An alternative route to compounds of formula I in which Y represents CHR$^2$—NR$^4$ is by cyclisation of compounds of formula (9):

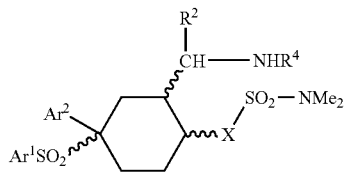

(9)

where Ar$^1$, Ar$^2$, X, R$^2$ and R$^4$ have the same meanings as before. The reaction takes place in refluxing tetrahydrofuran (THF), e.g. overnight. For this process, X is preferably CHR$^1$ or NR$^1$.

Compounds of formula (9) in which R$^2$ is H may be prepared by condensation of aldehydes (10) with R$^4$NH$_2$ and reduction of the resulting imine with sodium borohydride:

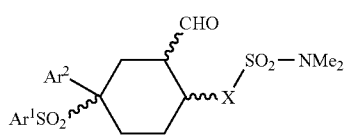

(10)

where Ar$^1$, Ar$^2$, X and R$^4$ have the same meanings as before. Both steps may carried out in ethanol solution at ambient temperature, and the first step is advantageously carried out in the presence of alumina.

Compounds of formula (9) in which R$^2$ is other than H may be prepared by reaction of aldehydes (10) with R$^4$NH$_2$ and reaction of the resulting imine with R$^2$—MgBr, e.g. in THF solution at 0° C.

The aldehydes (10) are available by oxidation of alcohols (11):

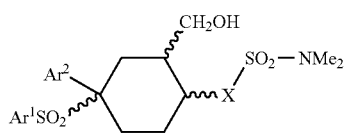

(11)

where Ar$^1$, Ar$^2$ and X have the same meanings as before. Suitable oxidation procedures include treatment with Dess-Martin periodinane in dichloromethane at ambient temperature.

Alcohols (11) are available by routes analogous to those described above for alcohols (1b).

Compounds of formula I in which Y is CHR²—CHR³ may be prepared by cyclisation of compounds (12):

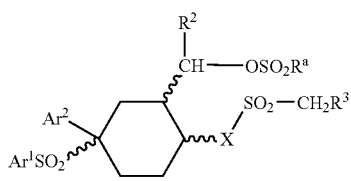

(12)

where Ar¹, Ar², X, R², R³ and Rᵃ have the same meanings as before. Preferably, X is NR¹ or CHR¹. The reaction takes place in THF at −30-20° C. in the presence of BuLi. Compounds (12) in which X is NR¹ or CHR¹ may be prepared by the same methods as described above for corresponding compounds (1a), substituting (respectively) R³CH₂SO₂Cl for R⁴NHSO₂Cl, and R¹CH₂SO₂CH₂R³ for R¹CH₂—SO₂N(R⁴)—CH₂CH═CH₂.

Compounds of formula I in which Y is CH₂—O and X is O may be prepared by sequential treatment of alcohols (1b) in which X is O, R² is H and R⁴ is H with methanesulphonyl chloride and sodium hydride. The first step is carried out in pyridine in the presence of 4-dimethylaminopyridine, and the second step in THF at ambient temperature.

Compounds of formula I in which Y is CH₂—O and X is NR¹ may be prepared by treatment of compounds (13a) with iodobenzene diacetate:

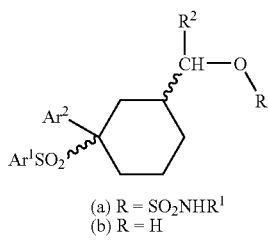

(13)

(a) R = SO₂NHR¹
(b) R = H where Ar¹, Ar², R¹ and R² have the same meanings as before. Most suitably, R¹ and R² are both H. The reaction takes place in refluxing dichloromethane in the presence of MgO and Rh(II)diacetate dimer. Compounds (13a) are available from the treatment of alcohols (13b) with R¹NHSO₂Cl in DMF at ambient temperature. Alcohols (13b) are obtained by treatment of aldehydes (14) with sodium borohydride (when R² is H) or with R²MgBr when R² is other than H:

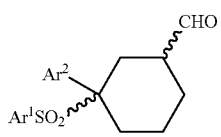

(14)

where Ar¹ and Ar² have the same meanings as before.

Aldehydes (14) may be prepared from enols (15) (WO 02/081435) in a process involving (i) formation of the methanesulphonate ester, (ii) reductive cleavage of the methanesulphonate group, and (iii) reduction of the carboxylate ester:

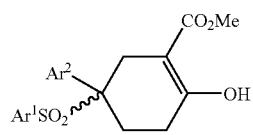

(15)

where Ar¹ and Ar² have the same meanings as before. Step (i) is carried out as described for the conversion of (1b) to (1a). Step (ii) involves treatment with sodium borohydride and nickel(II) chloride in a dichloromethane/methanol mixture at −10° C. Step (iii) involves treatment with diisobutylaluminium hydride in toluene at −78° C.

Compounds of formula I in which Y is CH═CH may be prepared by cyclisation of compounds of formula (16):

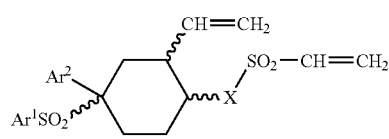

(16)

where X Ar¹ and Ar² have the same meanings as before. Preferably X is CHR¹ or NHR¹, most preferably NHR¹. The reaction takes place in dichloromethane in the presence of Grubb's catalyst. Compounds (16) may be prepared by the procedures described above for preparing compounds (1b), substituting chloroethanesulphonyl chloride for R⁴NHSO₂Cl, or R¹CH₂SO₂CH═CH₂ for R¹CH₂—SO₂N(R⁴)—CH₂CH═CH₂, followed by oxidation of the alcohol group and a Wittig reaction on the resulting aldehyde.

A preferred route to compounds of formula II in which R³ is other than H comprises alkylation of compounds (17) with R³ᵃ-L, followed by cleavage of the N-protecting group:

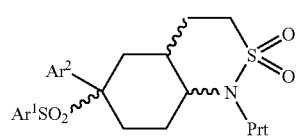

(17)

where R³ᵃ is R³ that is other than H, L is a leaving group such as halide (especially bromide or iodide), mesylate, tosylate or triflate, Prt is a protecting group such as p-methoxybenzyl, and Ar¹ and Ar² have the same meanings as before. The alkylation takes place in an aprotic solvent (such as THF) in the presence of strong base (such as lithium bis(trimethylsilyl)amide) at reduced temperature (e.g. −78° C.). When Prt is p-methoxybenzyl, cleavage may be effected by treatment with acid, e.g. trifluoroacetic acid at ambient temperature in an inert solvent such as dichloromethane.

A preferred route to compounds (17) involves cyclisation of sulfonamides (18):

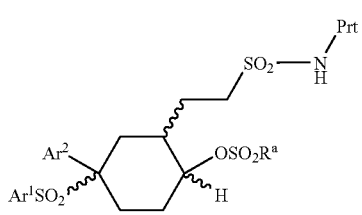
(18)

where $R^a$, $Ar^1$, $Ar^2$ and Prt have the same meanings as before. The cyclisation may be carried out by treatment with strong base such as sodium hydride in an aprotic solvent such as DMF at moderately elevated temperature (e.g. about 75° C.).

Compounds (18) are obtainable by reaction of sulfonyl chlorides (19) with PrtNH$_2$:

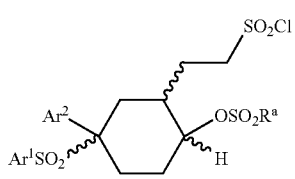
(19)

where $R^a$, $Ar^1$, $Ar^2$ and Prt have the same meanings as before. The reaction may be carried out in an inert solvent such as dichloromethane at about 0° C. using an excess of the amine.

Sulfonyl chlorides (19) are obtainable by reaction of sulfonates (20) with thiourea and treatment of the resulting adducts with chlorine:

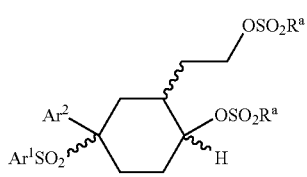
(20)

where $R^a$, $Ar^1$ and $Ar^2$ have the same meanings as before. The reaction with thiourea may be carried out in refluxing ethanol, and the resulting adduct may be treated with gaseous chlorine in aqueous acetic acid solution.

Sulfonates (20) are obtainable by treatment of diols (21) with $R^aSO_2Cl$ or $(R^aSO_2)_2O$:

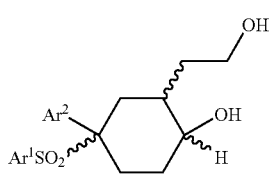
(21)

where $R^a$, $Ar^1$ and $Ar^2$ have the same meanings as before. The reaction is conveniently carried out in dichloromethane at about −10° C. in the presence of a base such as triethylamine.

Diols (21) are obtainable by sequential treatment of ketones (22) with ozone and sodium borohydride:

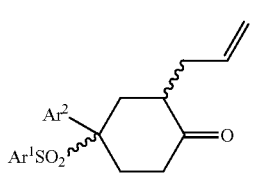
(22)

where $Ar^1$ and $Ar^2$ have the same meanings as before. The ozonolysis is typically carried out at about −78° C. in a dichloromethane/methanol mixture, then sodium borohydride added with warming to ambient temperature.

Ketones (21) are obtained by alkylation of cyclohexanones (5) with allyl bromide or allyl iodide under similar conditions to the conversion of (5) to (4).

Detailed procedures for the above-described routes are provided in the Examples section.

It will be apparent to those skilled in the art that individual compounds of formula I prepared by the above routes may be converted into other compounds in accordance with formula I by means of well known synthetic techniques such as alkylation, esterification, amide coupling, hydrolysis, coupling mediated by organometallic species, oxidation and reduction. Such techniques may likewise be carried out on precursors of the compounds of formula I. For example, substituents on the aromatic groups $Ar^1$ or $Ar^2$ may be added or interconverted by means of standard synthetic processes carried out on the compounds of formula I or their precursors. For example, a chlorine or bromine atom on $Ar^1$ or $Ar^2$ may be replaced by vinyl by treatment with vinyltributyltin in the presence of tri-t-butylphosphine, cesium fluoride and tris(dibenzylideneacetone)dipalladium(0). Ozonolysis of the vinyl group provides the corresponding formyl derivative, which may be transformed in a variety of ways, including oxidation to the corresponding acid, reduction to the corresponding benzyl alcohol, and conversion to the corresponding nitrile by treatment with hydroxylamine then triphenylphosphine and carbon tetrachloride. Procedures for transformations of this type are disclosed in WO 2004/031139. Similarly, alkenyl groups represented by $R^2$, $R^3$ or $R^4$ (such as allyl) may be subjected to ozonolysis to provide formyl derivatives, which in turn may be converted to other functional derivatives by standard routes, such as oxidation to carboxylic acids, reduction to primary alcohols, and conversion to nitriles as described above. The aforesaid alcohols may also be converted to the corresponding sulfonate esters and subjected to nucleophilic displacement by a variety of nucleophiles. The aforesaid nitrites may be hydrated to the corresponding primary amides by standard routes.

As a further example of this protocol, compounds of formula I (or their precursors) in which one or both of $R^1$ and $R^4$ represents H can be converted to the corresponding alkyl derivatives by standard alkylation methods. Similarly, compounds of formula I in which $R^2$ and $R^4$ represent vinyl or allyl may be converted to the corresponding compounds in which $R^2$ and $R^4$ complete a heterocyclic ring by treatment with Grubb's catalyst.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art. As an example of this strategy, prior to the cyclisation of compounds of formula (12) wherein X is NH, it is advantageous to protect the sulphonamide nitrogen by alkylation with allyl bromide. The allyl group may be removed subsequently by reduction with diisobutylaluminium hydride in toluene at ambient temperature in the presence of [Ph$_2$PCH$_2$CH$_2$CH$_2$PPh$_2$]NiCl$_2$.

An assay which can be used to determine the level of activity of compounds of the present invention is described in WO01/70677. A preferred assay to determine such activity is disclosed in WO 03/093252.

Alternative assays are described in *Biochemistry*, 2000, 39(30), 8698-8704.

See also, *J. Neuroscience Methods*, 2000, 102, 61-68.

The Examples of the present invention all had an ED$_{50}$ of less than 0.5 µM, typically less than 50 nM, in most cases less than 10 nM, and in preferred cases less than 1.0 nM, in at least one of the above assays.

The following examples illustrate the present invention. For convenience, compounds are typically depicted as being in accordance with formula IA regardless of their state of enantiomeric homogeneity. Homochiral compounds are indicated by means of the R and S configurational descriptors.

EXAMPLES

Intermediate 1

4-[(4-Chlorophenyl)sulfonyl]-4-(2,5-difluorophenyl)-2-[2-(trimethylsilyl)ethoxymethyl]cyclohexanone

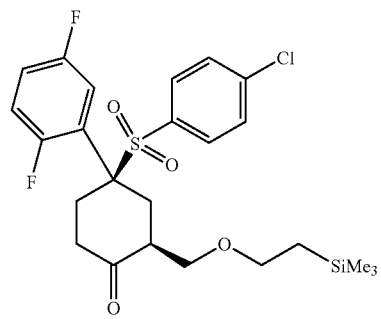

4-[(4-Chlorophenyl)sulfonyl]-4-(2,5-difluorophenyl)cyclohexanone (WO 02/081435) (2.0 g, 5.2 mmol) in dry tetrahydrofuran (10 mL) was added dropwise to a cooled solution of 0.5 M lithium hexamethyldisilazide in tetrahydrofuran (11.4 mL) at −78° C. The mixture was stirred at this temperature for 2 hours before adding 2-(trimethylsilyl)ethoxymethyl chloride (1.4 mL, 7.8 mmol) and the solution allowed to warm to rt. over 16 hours. The reaction mixture was diluted with ethyl acetate (10 mL), washed with water (10 mL), and the organic phase separated, dried (MgSO$_4$) and evaporated to dryness. The product was purified on silica eluting with [9:1] hexane-ethyl acetate to yield 1.2 g of the title compound. $^1$H NMR CDCl$_3$ 7.38 (4H, s), 7.24-7.16 (1H, m), 7.12-7.06 (1H, m), 6.97-6.87 (1H, m), 3.66 (1H, dd, J=9.7 and 3.0 Hz), 3.51-3.45 (3H, m), 3.17-3.15 (1H, m), 3.05-2.98 (1H, m), 2.56-2.49 (2H, m),241-2.35 (2H, m), 2.23-2.17 (1H, m), 0.91-0.87 (2H, m) and 0.03 (9H, s).

Intermediate 2

4-[(4-Trifluoromethylphenyl)sulfonyl]-4-(2,5-difluorophenyl)-2-[2-(trimethylsilyl) ethoxymethyl]cyclohexanone

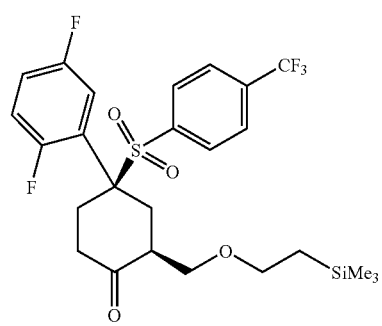

Prepared as for Intermediate 1, starting from 4-[(4-trifluoromethylphenyl)sulfonyl]-4 (2,5-difluorophenyl)cyclohexanone (WO 02/081435), and obtained as a solid. 16.3 g. $^1$H NMR CDCl$_3$ 7.69-7.59 (4H, m), 7.24-7.18 (1H, m), 7.12-7.06 (1 H, m), 6.93-6.86(1H, m), 3.67 (1H, dd, J=9.7 and 2.9 Hz), 3.58-3.47 (3H, m), 3.20-3.16 (1H, m), 3.04-2.98 (1H, m), 2.57-2.51 (2H, m), 2.41-2.38 (2H, m), 2.24-2.16 (1H, m), 0.91-0.87 (2H, m) and 0.03 (9H, s).

Intermediate 3

(R,S)-4-[(4-Trifluoromethylphenyl)sulfonyl]-4-(2,5-difluorophenyl)-2-[2-(trimethylsilyl) ethoxymethyl]cyclohexanone

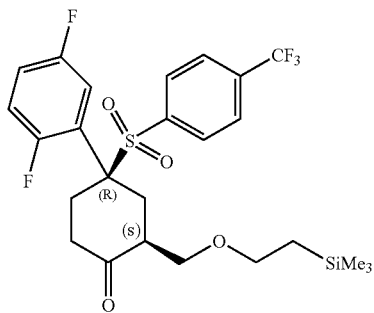

[(S-(R*, R*)]-(−)-Bis(α-methylbenzyl)amine (10 g, 44.4 mmol) and anhydrous lithium chloride (1.87 g, 44.5 mmol) were stirred in tetrahydrofuran (250 mL) under nitrogen gas, then cooled to −78° C. and treated slowly with butyllithium (1.6 mol solution in hexanes, 25.9 mL). The reaction mixture was allowed to warm up to 0° C. and stirred for 30 min. then re-cooled to an internal temperature of 100° C., stirring for 1 h. A solution of 4-[(4-trifluoromethylphenyl)sulfonyl]-4-(2, 5-difluorophenyl) cyclohexanone (WO 02/081435) (12.5 g, 29.9 mmol) in tetrahydrofuran (50 mL), cooled to −78° C., was added slowly, maintaining the internal temperature at −100° C. The mixture was stirred at −100° C. for 2 h., then 2-(trimethylsilyl) ethoxymethyl chloride (7.9 mL, 44.7 mmol) was added, the resulting mixture warmed to −78° C., and allowed to warm up slowly overnight to −12° C. The reaction mixture was quenched with a 1M solution of citric acid then extracted with ethyl acetate. The organic extracts were washed with a 1M citric acid, 5% sodium bicarbonate solution, dried (MgSO$_4$), filtered and the solvent was removed. The resulting oil was purified by column chromatography on silica gel eluting with 2 to 10% ethyl acetate: isohexane to give the title compound as a clear oil. Yield 5 g (30%).

$^1$H NMR (400 MHz, CDCl$_3$) δ 7.69 (2H, d, J 8.4 Hz), 7.60 (2H, d, J 8.4 Hz), 7.23-7.18 (1H, m), 7.15-7.08 (1H, m), 6.96-6.86 (1H, m), 3.70-3.64 (1H, m), 3.53-3.48 (3H, m), 3.22-3.16 (1H, m), 3.08-2.98 (1H, m), 2.61-2.51 (2H, m), 2.43-2.36 (2H, m), 2.25-2.14 (1H, m), 0.94-0.83 (2H, m), 0.00 (9H, s). Chiral purity determined by chiral HPLC.

Intermediate 4 (R, S)

(R,S)-4-[(4-Chlorophenyl)sulfonyl]-4-(2,5-difluorophenyl)-2-[2-(trimethylsilyl) ethoxymethyl]cyclohexanone

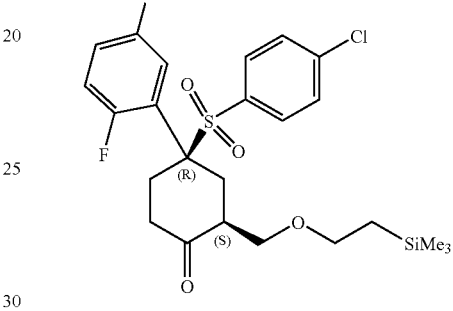

Prepared in the same manner as Intermediate 3 using the 4-[(4-chlorophenyl)sulfonyl]-4-(2,5-difluorophenyl )cyclohexanone as starting material. NMR data as for Intermediate 1.

Intermediate 5

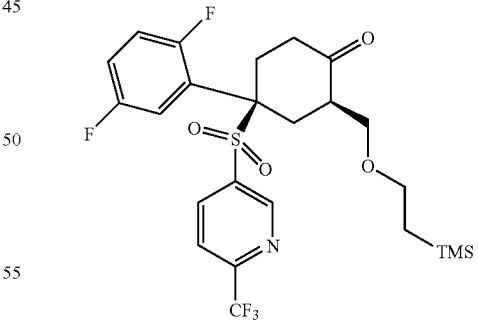

4-(2,5-Difluorophenyl)-4-(6-trifluoromethylpyridin-3-yl)cyclohexanone (WO 2004/031139) was converted to the desired product by the procedure described for Intermediate 1.

$^1$H NMR (360 MHz, CDCl$_3$) δ 0.01 (9H, s), 0.90 (2H, t, J=7.3 Hz), 2.14-2.25 (1H, m), 2.40-2.59 (4H, m), 3.01 (1H, m), 3.14-3.19 (1H, m), 3.48-3.53 (3H, m), 3.65-3.68 (1H, m), 6.87-6.95 (1H, m), 7.13-7.18 (1H, m), 7.23-7.28 (1H, m), 7.75 (1H, d, J=8.2 Hz), 7.95 (1H, d, J=6.4 Hz), 8.66 (1H, s).

Example 1

(4aSR,6RS,8aSR)-6-[(4-chlorophenyl)sulfonyl]-6-(2,5-difluorophenyl)-3-ethyloctahydro-1H-2,1,3-benzothiadiazine 2,2-dioxide

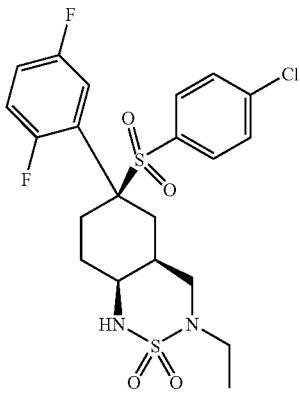

Step 1

4-[(4-Chlorophenyl)sulfonyl]-4-(2,5-difluorophenyl)-2-[2-(trimethylsilyl)ethoxymethyl]cyclohexanol (trans isomer)

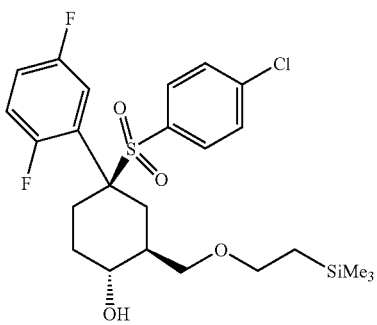

Intermediate 1 (23 g, 44.7 mmol) in isopropanol (2 L) was treated with NaBH$_4$ (6.8 g, 179 mmol) at −40° C. and stirred whilst allowing to warm to rt. over 16 hours. The reaction was quenched with 8% aqueous citric acid (1 L), diluted with ethyl acetate (1 L), then the organic phase was separated, dried (MgSO$_4$) and evaporated to dryness. The trans product was purified on silica eluting with hexane-ethyl acetate mixtures. Yield 23.3 g. $^1$H NMR CDCl$_3$ 7.39-7.31 (4H, m), 7.06-7.02 (2H, m), 6.86-6.83 (1H, m), 3.62-3.46 (5H, m), 2.90-2.42 (2H, m), 2.18-2.03 (2H, m), 1.91-1.80 (1H, m), 1.71-1.52 (1H, m), 1.24-1.20 (1H, m), 0.93-0.89 (2H, m), and 0.03 (9H, s).

Step 2

4-[(4-Chlorophenyl)sulfonyl]-4-(2,5-difluorophenyl)-2-[2-(trimethylsilyl)ethoxymethyl]cyclohexylamine

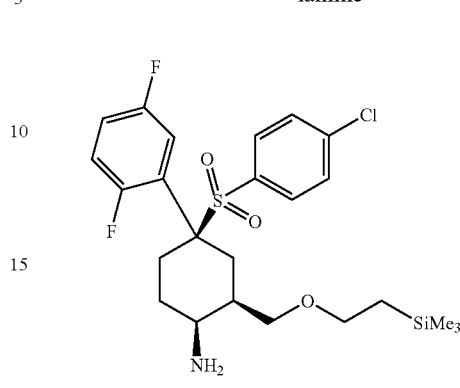

The alcohol from Step 1 (11.7 g, 22.7 mmol) in dichloromethane (100 mL) was treated with triethylamine (6.3 mL, 45 mmol) at 0° C. and stirred whilst methanesulphonyl chloride (2.2 mL, 27 mmol) was added. The reaction mixture was allowed to warm to r.t. over 1 hour, washed with water (20 mL), 10% aqueous citric acid (20 mL) and saturated aqueous sodium hydrogen carbonate (50 mL), then dried (MgSO$_4$) and evaporated to dryness. The residue was filtered through silica eluting with 20% ethyl acetate in hexanes to give the mesylate (10 g).

This solid in dimethylformamide (50 mL) was treated with sodium azide (1.4 g, 29 mmol) and heated to 95° C. for 8 hrs. The mixture was treated with water (80 mL) and extracted with ethyl acetate (2×50 mL). The combined organics were washed with brine, dried (MgSO$_4$) and evaporated to dryness. The residue (8 g, 14.7 mmol), in tetrahydrofuran (320 mL) and water (32 mL), was treated with triphenylphosphine (4.7 g, 18 mmol) at room temperature for 15 mins and then the mixture was heated at reflux for 4 hrs. The mixture was allowed to cool to rt. and then passed through SCX Varian Bond Elut™ cartridge. The basic fraction was evaporated to give the primary amine (7.2 g). $^1$H NMR CDCl$_3$ 7.39-7.31 (4H, m), 7.09-6.96 (2H, m), 6.85-6.80 (1H, m), 3.48-3.15 (5H, m), 2.93-2.29 (4H, m), 1.74-1.19 (3H, m), 0.93-0.89 (2H, m), and 0.03 (9H, s).

MS MH+ 516(518).

Step 3

4-[(4-Chlorophenyl)sulfonyl]-4-(2,5-difluorophenyl)-2-(hydroxymethyl)cyclohexylamine

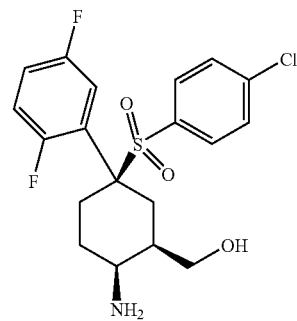

The product of Step 2 (5.5 g, 10.6 mmol) in dichloromethane (40 mL) was treated with boron trifluoride etherate (4 mL) and after 2 hours the mixture was cooled to 0° C. and stirred during the addition of sodium hydroxide (2.5M, 20 mL). The layers were separated and the organics were washed with brine, dried (MgSO$_4$) and evaporated to give an oil which was azeotroped with heptane to give the amino alcohol as a white solid (5.8 g) MS ES+ 416, 418.

Step 4

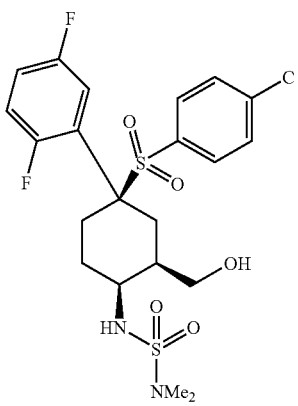

The product of Step 3 (5.3 g, 10 mmol) in dichloromethane (40 mL) and dimethyl acetamide (40 mL) was treated with triethylamine (3.4 mL, 24 mmol) and then with N,N-dimethylsulphamoyl chloride (1.6 mL, 14.5 mmol). After 72 hours the mixture was quenched by the addition of water (200 mL). The mixture was extracted with dichloromethane (2×100 mL) and the organics were washed with brine, dried (MgSO$_4$) and evaporated to give an oil which was filtered through silica to give the sulphamide (4 g). $^1$H NMR CDCl$_3$ 7.38-7.31 (4H, m), 7.07-7.04 (2H, m), 6.85-6.79 (1H, m), 5.24 (1H, d, J=11 Hz), 3.79-3.65 (2H, m), 3.58-3.50 (1H, m), 2.98-2.92 (1H, m), 2.83 (6H, s), 2.58-2.20 (3H, m), 2.09-1.98 (2H, m), and 1.56-1.52 (1H, m).

Step 5

The product of Step 4 (0.1 g, 0.2 mmol) in dichloromethane (3 mL) was treated with Dess-Martin periodinane (89 mg, 0.22 mmol) and after 1 hour the mixture was quenched by the addition of 10% aqueous sodium metabisulfite (2 mL). After stirring for 10 mins, the layers were separated, the aqueous layer was extracted with dichloromethane (2×10 mL) and the combined organics were washed with saturated aqueous sodium bicarbonate, brine, dried (MgSO$_4$) and evaporated, azeotroping with heptane, to give the solid aldehyde (0.1 g). The crude aldehyde was dissolved in ethanol (3 mL) and treated with 2M ethylamine in ethanol (10 eq, 1 mL), and oven dried alumina (100 mg) was added. The mixture was stirred over 16 hours then filtered. Sodium borohydride (36 mg, 1 mmol) was added and after one hour the solvent was removed in vacuo. The residue was partitioned between ethyl acetate (5 mL) and saturated aqueous sodium bicarbonate (5 mL). The organics were dried (Na$_2$SO$_4$) and evaporated, and the residue dissolved in tetrahydrofuran (5 mL) and refluxed overnight. The solvent was removed in vacuo and the residue was chromatographed on silica gel eluting with 25% ethyl acetate in hexane to give the desired cyclic sulphamide (50 mg). $^1$H NMR CDCl$_3$ 7.39-7.30 (4H, m), 7.11-7.06 (2H, m), 6.90-6.83 (1H, m), 4.44 (1H, d, J=11 Hz), 3.86-3.83 (1H, m), 3.46 (1H, dd, J=12.5 and 3.5 Hz), 3.40 (1H, m), 3.00-2.93 (2H, m), 2.72-2.67 (1H, m), 2.62-2.45 (2H, m), 2.17-2.11 (1H, m), 1.96-1.92 (1H, m), 1.68-1.55 (2H, m) and 1.33-1.30 (3H, m),

MS ES$^-$ 503, 505.

The following were prepared by the same procedure, substituting the appropriate amine for ethylamine in Step 5:

| Example | R | MS (ES−) |
| --- | --- | --- |
| 2 | n-propyl | 517, 519 |
| 3 | n-butyl | 531, 533 |
| 4 | cyclopropyl | 515, 517 |
| 5 | cyclopentyl | 543, 545 |
| 6 | sec-butyl | 531, 533 |
| 7 | cyclopropylmethyl | 529, 531 |
| 8 | t-butyl | 531, 533 |
| 9 | 2,2,2-trifluoroethyl | 557, 559 |
| 10 | 2-hydroxyethyl | 519, 521 |
| 11 | methyl | 489, 491 |
| 12 | isopropyl | 517, 519 |
| 13 | cyclobutyl | 529, 531 |
| 14 | 2-fluoroethyl | 521, 523 |

Examples 15-25

Following the procedure of Example 1, starting from Intermediate 2 and using the appropriate amine in Step 4, there were prepared:

| Example | R | MS (ES−) |
| --- | --- | --- |
| 15 | ethyl | 537 |
| 16 | methyl | 523 |
| 17 | i-propyl | 551 |
| 18 | cyclopropyl | 549 |
| 19 | cyclobutyl | 563 |
| 20 | t-butyl | 565 |

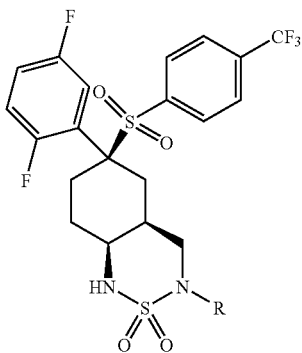

| Example | R | MS (ES−) |
|---|---|---|
| 21 | 2,2,2-trifluoroethyl | 591 |
| 22 | 2-hydroxyethyl | 553 |
| 23 | 2-fluoroethyl | 555 |
| 24 | 2-cyanoethyl | 562 |
| 25 | 2-methoxyethyl | 567 |

Example 26

(4RS,4aRS,6RS,8aSR)-3,4-diallyl-6-[(4-chlorophenyl)sulfonyl]-6-(2,5-difluorophenyl) octahydro-1H-2,1,3-benzothiadiazine 2,2-dioxide

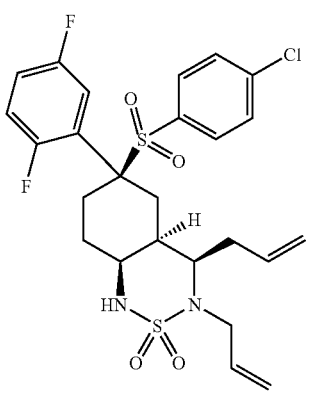

The product of Example 1 Step 4 (0.25 g, 0.5 mmol) in dichloromethane (10 mL) was treated with Dess-Martin periodinane (243 mg, 0.57 mmol) and after 1 hour the mixture was quenched with 10% aqueous sodium metabisulfite (5 mL). After stirring for 10 minutes the layers were separated, the aqueous layer extracted with dichloromethane (2×25 mL) and the combined organics were washed with saturated aqueous sodium bicarbonate, brine, dried (MgSO₄) and evaporated, azeotroping with heptane to give the aldehyde as a solid (0.25 g). The crude aldehyde was dissolved in acetonitrile (5 mL), and allylamine (75 μL, 1 mmol) and alumina (100 mg) were added. After 2 hours the mixture was filtered, evaporated, and the residue dissolved in dry tetrahydrofuran (8 mL). The solution was cooled to 0° C. and then 1M allyl magnesium bromide in tetrahydrofuran (1 mL, 1 mmol) was added. After 16 hours the mixture was treated with acetic acid (1 drop), and then washed with sat. aqueous sodium hydrogen carbonate (10 mL). The aqueous layer was extracted with ethyl acetate and the combined organics were washed with brine, dried (MgSO₄) and concentrated. The residue was then dissolved in tetrahydrofuran and refluxed for 16 hours to effect cyclisation. The solvent was removed in vacuo and the product was purified by column chromatography on silica eluting with 15% ethyl acetate in hexanes to give the desired product (195 mg). ¹H NMR CDCl₃ 7.39 (2H, d, J=9 Hz), 7.30 (2H, d, J=9 Hz), 7.11-6.92 (2H, m), 6.90-6.83 (1H, m), 5.85-5.78 (1H, m), 5.59-5.49 (1H, m), 5.34-5.31 (2H, m), 5.02-4.92 (2H, m), 4.53 (1H, d, J=11 Hz), 4.26-4.19 (1H, m), 3.99-3.96 (1H, m), 3.58-3.52 (1H, m), 3.16-3.14 (1H, m), 2.72-2.18 (6H, m), 1.96-1.92 (1H, m) and 1.68-1.55 (1H, m). MS ES⁻ 555, 557.

Example 27

(2RS,4aSR,11aRS,11bRS)-2-[(4-chlorophenyl)sulfonyl]-2-(2,5-difluorophenyl)-1,2,3,4,4 a,5,8,11,11a,11b-decahydropyrido [1,2-c][2,1,3]benzothiadiazine 6,6-dioxide

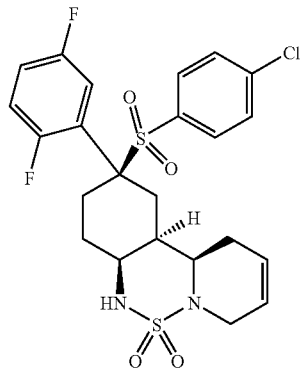

The product of Example 26 (190 mg, 0.34 mmol) in dichloromethane (5 mL) was treated with Grubb's catalyst (2ⁿᵈ generation) (1 mg). The mixture was stirred for 24 h, then evaporated and the residue was purified by column chromatography on silica eluting with 20% ethyl acetate in hexanes to give Example 27 (150 mg). ¹H NMR CDCl₃ 7.39 (2H, d, J=9 Hz), 7.31 (2H, d, J=9 Hz), 7.11-7.01 (2H, m), 6.90-6.83 (1H, m), 5.83-5.79 (1H, m), 5.61-5.55 (1H, m), 4.89 (1H, d, J=11 Hz), 4.32-4.28 (1H, m), 4.08-4.05 (1H, m), 3.71-3.64 (1H, m), 3.49-3.46 (1H, m), 2.78-2.25 (5H, m), 2.06-2.01 (2H, m), 1.82-1.75 (1H, m) and 1.50-1.45 (1H, m). MS ES⁻ 527, 529.

Example 28

(2RS,4aSR,11aRS,11bRS)-2-[(4-chlorophenyl)sulfonyl]-2-(2,5-difluorophenyl)dodecahydropyrido[1,2-c][2,1,3]benzothiadiazine 6,6-dioxide

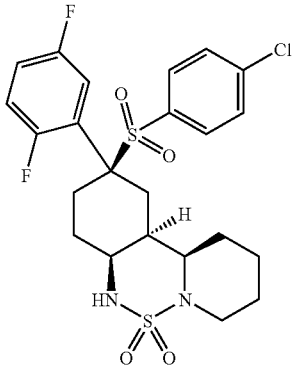

The product from Example 27 (16 mg, 0.03 mmol) in ethyl acetate (2 mL) was treated with 10% palladium on carbon [1 mg] and hydrogen gas (1 atm.). The mixture was stirred for 2 hrs and then filtered and evaporated to give Example 28 (15 mg). $^1$H NMR CDCl$_3$ 7.39 (2H, d, J=9 Hz), 7.32 (2H, d, J=9 Hz), 7.11-7.01 (2H, m), 6.90-6.83 (1H, m), 5.03 (1H, d, J=11 Hz), 4.02-3.98 (2H, m), 3.20-3.15 (1H, m), 2.95-2.88 (1H, m), 2.72-2.18 (5H, m), 2.03-1.95 (2H, m), 1.90-1.81 (2H, m) and 1.65-1.49 (4H, m). MS ES$^-$ 529, 531.

Example 29

(4RS,4aRS,6RS,8aSR)-4-allyl-6-[(4-chlorophenyl)sulfonyl]-6-(2,5-difluorophenyl)-3-isoproploctahydro-1H-2,1,3-benzothiadiazine 2,2-dioxide

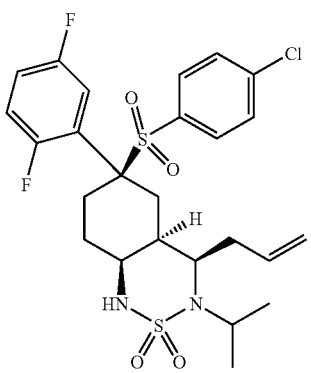

Prepared by the procedure of Example 26, substituting isopropylamine for allylamine. $^1$H NMR CDCl$_3$ 7.39 (2H, d, J=8 Hz), 7.30 (2H, d, J=8Hz), 7.10-7.01 (2H, m), 6.89-6.85 (1H, m), 5.59-5.49 (1H, m), 5.02-4.90 (2H, m), 4.36 (1H, d, J=11 Hz), 4.16-4.13 (1H, m), 3.97-3.95 (1H, m), 3.14-3.12 (1H, m), 2.77-2.70 (1H, m), 2.56-2.15 (5H, m), 1.96-1.92 (1H, m), 1.68-1.55 (2H, m) and 1.34-1.24 (6H, m). MS ES$^-$557, 559.

Example 30

(4RS,4aRS,6RS,8aSR)-6-[(4-chlorophenyl)sulfonyl]-6-(2,5-difluorophenyl)-3-isopropyl-4-propyloctahydro-1H-2,1,3-benzothiadiazine 2,2-dioxide

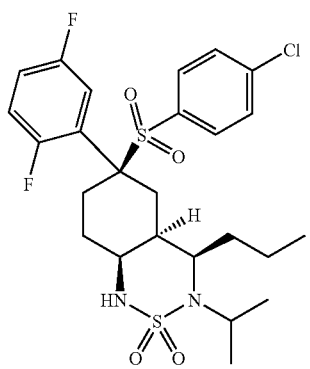

The product of Example 29 (16 mg, 0.03 mmol) was dissolved in ethyl acetate (2 mL) and treated with 10% palladium on carbon (1 mg). The mixture was stirred for 2 hrs under an atmosphere of hydrogen and then filtered and evaporated to give Example 30 (15 mg). $^1$H NMR CDCl$_3$ 7.39 (2H, d, J=8 Hz), 7.30 (2H, d, J=8Hz), 7.12-7.05 (2H, m), 6.89-6.85 (1H, m), 4.30 (1H, d, J=11 Hz), 4.15-4.10 (1H, m), 3.97-3.95 (1H, m), 3.04-3.02 (1H, m), 2.56-2.15 (3H, m), 1.98-1.92 (2H, m), 1.72-1.58 (4H, m), 1.34-1.24 (6H, m), 1.21-1.10 (2H, m) and 0.94-0.86 (3H, m). MS ES$^-$ 559, 561.

Example 31

(4aRS,6RS,8aSR)-6-[(4-chlorophenyl)sulfonyl]-6-(2,5-difluorophenyl)octahydro-3,2,1-benzoxathiazine 2,2-dioxide

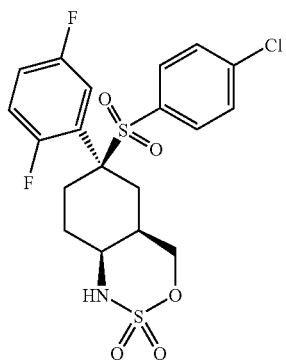

Step 1:

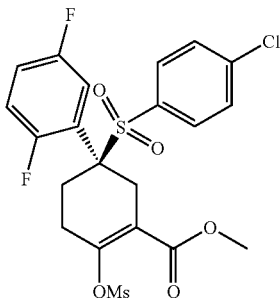

The enol from Example 1 of WO 02/081435 (18.4 g, 420 mmol) in dichloromethane (100 mL) at 0° C. was treated with triethylamine (8.7 mL, 620 mmol) and after 0.25 h. with methanesulphonyl chloride (4.0 mL, 0.530 mmol). After stirring for 1 h. at r.t., water was added and the organics extracted into dichloromethane (3×). The organic extract was dried (MgSO$_4$), solvent removed in vacuo and the crude product purified by silica gel chromatography eluting with 30% ethyl acetate/hexane to give product as a white foam (19.5 g, 90%).

Step 2:

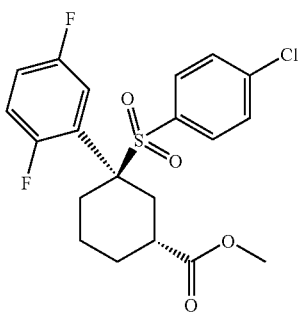

The mesylate from Step 1 (200 mg, 0.35 mmol) was dissolved in methanol/dichloromethane (10 mL) (5:1) and cooled to −10° C. Nickel chloride hexahydrate (82 mg, 0.35 mmol) was added, followed by sodium borohydride (67 mg, 1.8 mmol) in one portion. After stirring at −10° C. for 2 h the reaction was filtered through Celite™ and washed with methanol. Solvent was removed in vacuo and the residue dissolved in ethyl acetate, washing with 2M hydrochloric acid (2×), water (2×) and brine (2×). The organic extract was dried (MgSO$_4$) and solvent removed in vacuo. The crude product was purified by silica gel chromatography eluting with 20% ethyl acetate/hexane to give desired product (31 mg, 21%). $^1$H NMR (400 MHz CDCl$_3$) δ 1.63-1.65 (1H, m), 1.84-1.89 (2H, m), 2.00-2.18 (2H, m), 2.50-2.56 (1H, m), 2.70 (1H, m), 2.93-2.95 (1H, m), 3.22-3.24 (1H, m), 3.55 (3H, s), 6.73-6.80 (1H, m, Ar—H), 6.97-7.01 (1H, m, Ar—H), 7.07-7.12 (1H, m, Ar—H), 7.28-7.37 (4H, m, Ar—H).

Step 3:

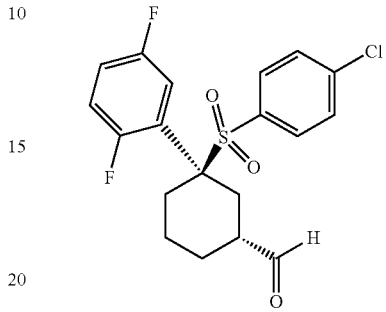

The foregoing ester (3.0 g, 7 mmol) was dissolved in toluene (50 mL) and cooled to −78° C. Diisobutylaluminium hydride (1.0 M in toluene) (8.7 mmol, 8.7 mL) was added over a 0.5 h period, the reaction stirred at −78° C. for 1.5 h, then quenched with methanol (0.5 mL), 2N sodium hydroxide (1 mL) and water (2 mL). The reaction mixture was warmed to r.t. and filtered through Celite™, washing with ethyl acetate (500 mL). The organic extracts were washed with water (2×), brine (2×) then dried (MgSO$_4$) and the solvent was removed in vacuo. The crude product was purified by silica gel chromatography eluting with 10% ethyl acetate/hexane and the aldehyde obtained as a white solid (1.86 g, 67%). $^1$H NMR (400 MHz CDCl$_3$) δ 1.62-1.74 (2H, m), 1.80 (1H, m), 2.01-2.08 (1H, m), 2.16-2.22 (1H, m), 2.61-2.75 (2H, m), 2.94-2.99 (1H, m), 3.06-3.12 (1H, m), 6.77-6.83 (1H, m, Ar—H), 6.98-7.06 (2H, m, Ar—H), 7.29-7.38 (4H, m, Ar—H), 9.57 (1H, s, CHO).

Step 4:

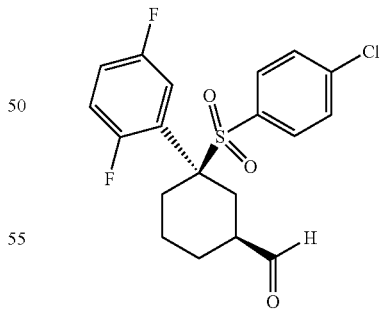

The aldehyde from Step 3 (1.86 g, 4.3 mmol) in dichloromethane/methanol (45 mL) (1:2) was treated with potassium carbonate (6.1 g, 43 mmol) and the mixture was stirred at rt. for 2 h., diluted with dichloromethane (50 mL) and washed with water (3×). The organic extracts were dried (MgSO$_4$); and solvent removed in vacuo to give epimerised aldehyde as a white crystalline solid (1.8 g, 97%). $^1$H NMR (400 MHz CDCl$_3$) δ 1.27-1.39 (2H, m), 1.96-2.07 (4H, m), 2.16-2.19 (1H, m), 2.71-3.1 (2H, m), 6.83-6.90 (1H, m, Ar—H), 7.03-7.09 (2H, m, Ar—H), 7.35-7.40 (4H, m, Ar—H), 9.61 (1H, s, CHO).

Step 5:

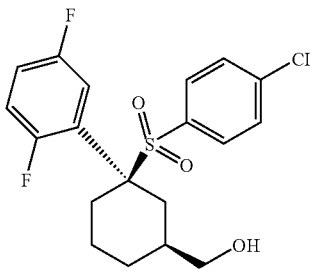

The aldehyde (1.0 g, 2.5 mmol) was suspended in methanol (20 mL) and cooled to 0° C. Sodium borohydride (48 mg, 1.25 mmol) was added in one portion and reaction stirred for 1 h. The solvent was removed in vacuo and the crude product was purified by silica gel chromatography eluting with 20% ethyl acetate/hexane. The alcohol was obtained as a colourless oil (0.9 g, 90%). $^1$H NMR (400 MHz CDCl$_3$) δ 1.3-1.5 (2H, m), 1.70 (1H, m), 1.83-1.90 (2H, m), 2.07 (1H, m), 2.60-3.0 (2H, m), 3.50-3.53 (2H, m), 6.80-6.87 (1H, m, Ar—H), 7.01-7.11 (2H, m, Ar—H), 7.36-7.39 (4H, m, Ar—H).

Step 6:

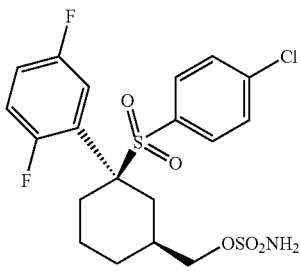

The alcohol (150 mg, 0.13 mmol) was dissolved in N,N-dimethylformamide (3 mL) and sulphamoyl chloride (150 mg, 0.39 mmol) was added. The reaction was stirred at rt. for 4 h then dissolved in ethyl acetate (50 mL) and washed with water (3×). The organic layer was dried (MgSO$_4$) and solvent removed in vacuo. The residue was purified by silica gel chromatography eluting with 40% ethyl acetate/hexane to give a white solid (90 mg, 50%). $^1$H NMR (400 MHz CDCl$_3$) δ 1.19-1.27 (2H, m), 1.70-1.72 (2H, m), 1.86-1.97 (2H, m), 2.04 (1H, s), 2.5-3.0 (2H, m), 4.03-4.1 (2H, m), 5.0 (2H, s, NH$_2$), 6.85 (1H, s, Ar—H), 7.02-7.08 (2H, m, Ar—H), 7.35-7.39 (4H, m, Ar—H). MS ES$^-$ 478.

Step 7

The sulphamate from Step 6 (90 mg, 0.19 mmol) was dissolved in dichloromethane (3 mL) and magnesium oxide (17 mg, 0.43 mmol) added, followed by iodobenzene diacetate (7 mg, 0.2 mmol) and rhodium (II) acetate dimer (1 mg). The mixture was heated at 40° C. for 0.5 h, solvent was removed in vacuo and the crude product purified by silica gel chromatography eluting with 40% ethyl acetate/hexane, followed by preparative HPLC to give a 9:1 mix of diastereomers, the major component being the title compound (7 mg, 8%). $^1$H NMR (500 MHz CDCl$_3$) δ 1.51-1.53 (1H, m), 1.71-1.74 (1H, m), 1.93-1.96 (1H, m), 2.28-2.30 (1H, m), 2.55-2.65 (2H, m), 2.72-2.76 (1H, m), 3.92 (1H, s), 4.30-4.32 (1H, d, J=11.6 Hz), 4.64-4.66 (1H, d, J=8.8 Hz, NH), 4.99-5.01 (1H, d, J=10.7 Hz), 6.84-6.89 (1H, m, Ar—H), 7.07-7.12 (2H, m, Ar—H), 7.32-7.41 (4H, m, Ar—H). MS ES$^-$ 476/478.

Example 32

(4aSR,6RS,8aSR)-6-[(4-chlorophenyl)sulfonyl]-6-2,5-difluorophenyl)octahydro-1,2,3-benzoxathiazine 2,2-dioxide

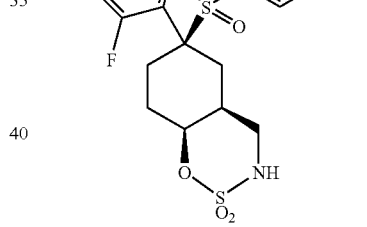

Step 1

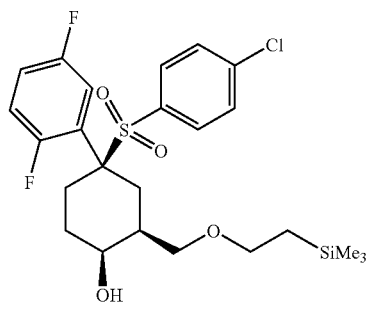

Intermediate 1 (14.8 g, 28.7 mmol) in dry THF (500 mL) cooled to −78° C. was treated dropwise with L-Selectride (1M in THF, 34.5 mL, 34.5 mmol). The mixture was stirred at this temperature for 1.5 h and then quenched with hydrochloric acid (2M, 50 mL), allowed to warm to room temperature and concentrated to half volume. The residue was diluted with water and extracted with ethyl acetate (3×100 mL). The organics were washed with brine, dried (MgSO$_4$), filtered and evaporated. The crude product was purified by flash chromatography (5:1 isohexane/ethyl acetate to 2:1) to give a white solid (12.1 g).

$^1$H NMR CDCl$_3$ −0.03 (9H, s), 0.98-0.82 (4H, m), 1.45-1.29 (4H, m), 1.91-1.84 (1H, brs), 2.61-2.57 (2H, m), 3.18 (1H, br), 3.55-3.41 (3H, m), 6.91-6.80 (1H, m), 7.14-6.98 (2H, m), 7.35 (4H, s).

Step 2

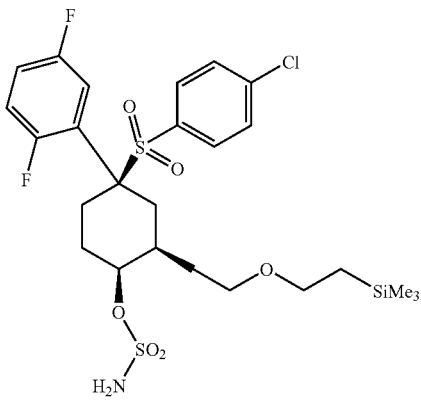

The product from Step 1 (980 mg, 1.9 mmol) was dissolved in N,N-dimethylacetamide (15 mL) and sulphamoyl chloride (875 mg, 7.6 mmol) was added in one portion. The reaction was heated at 50° C. overnight, allowed to cool and diluted with water (150 mL). After extraction with ethyl acetate (3×50 mL), the organics were washed with brine, dried (MgSO$_4$), filtered and evaporated. The crude product was purified by flash chromatography (5:1 isohexane/ethyl acetate to 2:1) to give a white foam (720 mg).

MS MH−594

Step 3

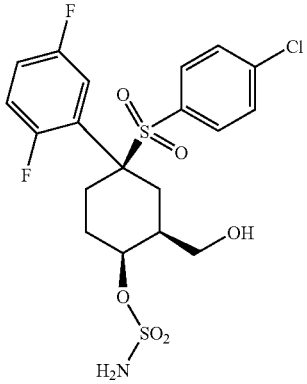

Prepared from the product of Step 2 by the procedure of Example 1 Step 3.

MS ES− 494

Step 4

The alcohol from Step 3 (900 mg, 1.81 mmol) in dry pyridine (5 mL) was treated with N,N-dimethylaminopyridine (110 mg, 0.6 mmol) and p-toluenesulfonyl chloride (1.0 g, 5.4 mmol) and the reaction stirred overnight at 40° C. The mixture was diluted with water (50 mL) and extracted with ethyl acetate (3×50 mL). The organics were washed with 2M hydrochloric acid (×2), water, brine, dried (MgSO$_4$), filtered and evaporated. The crude tosylate was purified by flash chromatography (4:1 isohexane/ethyl acetate to 1:1) to give a white solid (910 mg).

To this tosylate (660 mg, 1.15 mmol) in dry THF (8 mL) was added sodium hydride (60% dispersion, 60 mg, 1.5 mmol). The reaction was allowed to stir overnight, then quenched with saturated aqueous ammonium chloride (5 mL), diluted with water (50 mL) and extracted with ethyl acetate (3×50 mL). The organics were washed with brine, dried (MgSO$_4$), filtered and evaporated. The crude product was purified by flash chromatography (9:1 dichloromethane/methanol) to give the desired product as a white foam (520 mg). $^1$H NMR (MeOD) 0.82-0.91 (3H, m), 1.52-1.72 (2H, m), 2.03-2.08 (1H, m), 2.34-2.74 (4H, m), 3.72 (1H, dd, J=3.4, 14.7 Hz), 6.97-7.04 (1H, m), 7.18-7.23 (2H, m), 7.40 (2H, d, J=8.7 Hz), 7.51 (2H, d, J=8.7 Hz)

Example 33

(4aSR,6RS,8aSR)-6-[(4-chlorophenyl)sulfonyl]-6-(2,5-difluorophenyl)-3-methyloctahydro-1,2,3-benzoxathiazine 2,2-dioxide

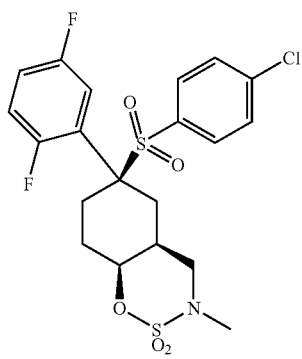

To the product of Example 32 (40 mg, 0.083 mmol) in dry THF (2 mL) was added sodium hydride (60% dispersion, 4 mg, 0.1 mmol) followed by iodomethane (8 µl, 0.17 mmol). The mixture was allowed to stir overnight, quenched with saturated aqueous ammonium chloride (10 mL) and extracted with ethyl acetate (3×50 mL). The organics were washed with brine, dried (MgSO$_4$), filtered and evaporated. The crude product was purified by flash chromatography (2:1 isohexane/ethyl acetate) to give a white solid (34 mg).

$^1$H NMR CDCl$_3$ 1.43 (1H, s), 1.67-1.75 (1H, m), 2.20 (1H, dd, J=2.9, 15.4 Hz), 2.44-2.64 (3H, m), 2.86 (3H, s), 2.89-2.99 (2H, m), 3.55 (1H, dd, J=3.2, 12.7 Hz), 4.90 (1H, s), 6.85-6.91 (1H, m), 7.02-7.12 (2H, m), 7.35 (2H, d, J=8.5 Hz), 7.37 (2H, d, J=8.5 Hz).

Examples 34-37

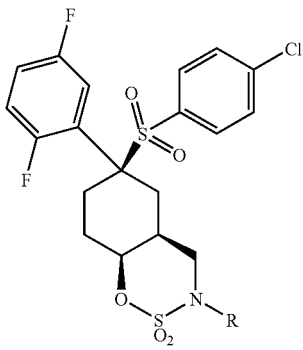

Following the procedure of Example 33, substituting the appropriate alkyl halide for iodomethane and refluxing the reaction mixture for 5 hours, the following were prepared:

| Example | R |
|---------|---|
| 34 | ethyl |
| 35 | n-propyl |
| 36 | allyl |
| 37 | cyclopropylmethyl |

Example 28

(4aSR,6RS,8aSR)-6-[(4-chlorophenyl)sulfonyl]-3-cyclobutyl-6-(2,5-difluorophenyl)octahydro-1,2,3-benzoxathiazine 2,2-dioxide

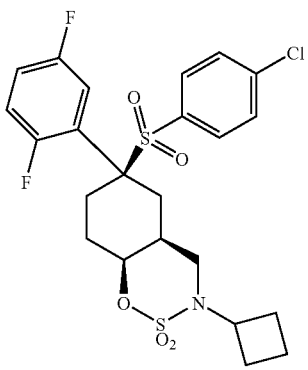

Steps 1-4 of Example 32 were repeated, using cyclobutylsulfamoyl chloride in place of sulphamoyl chloride in Step 2. Cyclisation was effected as in Step 5 of Example 32 except the reaction was performed at reflux.

$^1$H NMR CDCl$_3$ 1.55 (2H, m), 1.65-1.89 (2H, m), 2.14-2.17 (2H, m), 2.17 (1H, m), 2.27-2.99 (6H, m), 3.00-3.09 (1H, m), 3.34-3.37 (1H, m), 3.86-3.93 (1H, m), 4.84 (1H, s), 6.80-7.09 (3H, m), 7.35 (2H, d, J=8 Hz), 7.39-7.41 (2H, d, J=8 Hz).

Example 39

(4aSR,6RS,8aSR)-6-[(4-chlorophenyl)sulfonyl]-6-(2,5-difluorophenyl)hexahydro-4H-1,3,2-benzodioxathline 2,2-dioxide

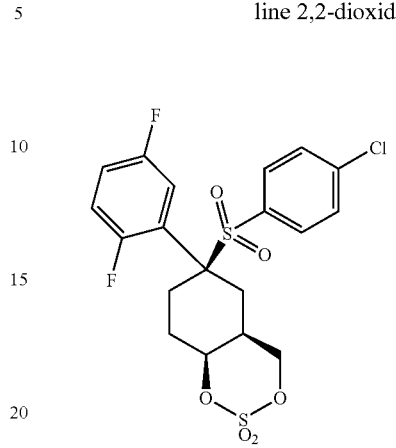

Step 4 of Example 32 was repeated, substituting methanesulfonyl chloride for toluenesulfonyl chloride. Treatment of the crude mesylate by the procedure of Example 32 Step 5 provided the sulfate rather than the sulfamate.

$^1$H NMR CDCl$_3$ 1.45-1.52 (1H, m), 1.94 (1H, s), 2.55-2.67 (4H, m), 3.02-3.10 (1H, m), 3.95 (1H, dd, J=1.2, 5.6 Hz), 4.73 (1H, t, J=4.6 Hz), 4.79 (1H, t, J=5.3 Hz), 6.83-6.88 (1H, m), 6.99-7.07 (2H, m), 7.38-7.42 (4H, m).

Example 40

(4aSR,6RS,8aSR)-3-cyclopropyl-6-(2,5-difluorophenyl)-1-methyl-6-{[4-(trifluoromethyl)phenyl]sulfonyl}octahydro-1H-2,1,3-benzothiadiazine 2,2-dioxide

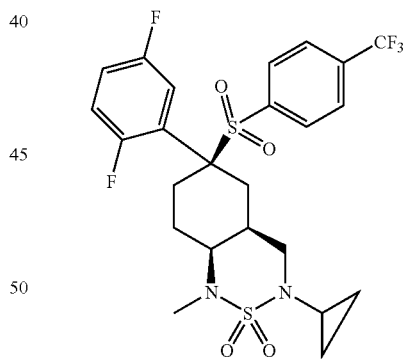

The product of Example 18 (7 mg, 0.012 mmol) was dissolved in dimethyl formamide (1 mL) and sodium hydride (60% suspension in mineral oil, 3 mg) was added. The mixture was heated to 90° C. for 2 hours before adding methyl iodide (8 µL), heating at 50° C. for 3 hours, then pouring into ethyl acetate (20 mL) and washing with water (3×30 mL). The organic phase was dried and evaporated to give an oil which was purified by preparative t.l.c. to give the desired product.

$^1$H NMR CDCl$_3$ 7.69-7.52 (4H, m), 7.12-7.07 (2H, m), 6.87-6.80 (1H, m), 3.78-3.72 (1H, m), 3.49-3.48 (1H, m), 3.13-3.07 (2H, m), 2.76 (3H, s), 2.68-2.63 (1H, m), 2.60-2.35 (3H, m), 2.21-2.17 (1H, m), 1.65-1.59 (1H, m), 1.45-1.35 (1H, m), 0.95-0.83 (2H, m) and 0.78-0.72 (2H, m).

Examples 41 and 42

(4aS,6R,8aS)-6-[(4-chlorophenyl)sulfonyl]-3-cyclopropyl-6-(2,5-difluorophenyl)octahydro-1H-2,1,3-benzothiadiazine 2,2-dioxide and (4aR,6S,8aR)-6-[(4-chlorophenyl)sulfonyl]-3-cyclopropyl-6-(2,5-difluorophenyl) octahydro-1H-2,1,3-benzothiadiazine 2,2-dioxide

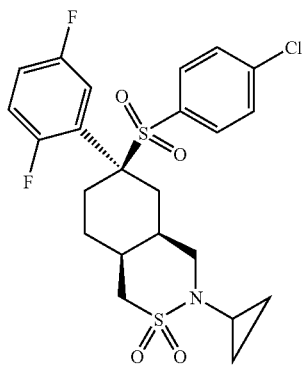

and

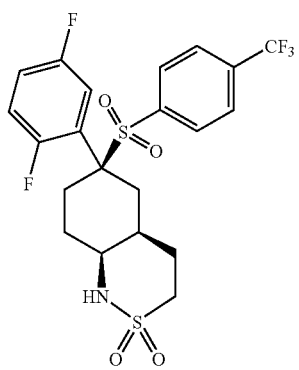

The product from Example 4 (5 mg) was separated by chiral HPLC into its constituent enantiomers using a CHIRACEL OD-H (250×4.5 mm) column eluting with 15% ethanol in isohexanes (2 mL/min) to give Example 41 (2 mg) and Example 42 (2 mg) MS (ES⁻) 515, 517.

Example 43

(4aRS,6RS,8aSR)-6-(2,5-difluorophenyl)-6-{[4-(trifluoromethyl)phenyl]sulfonyl}octahydro-1H-2,1-benzothiazine 2,2-dioxide

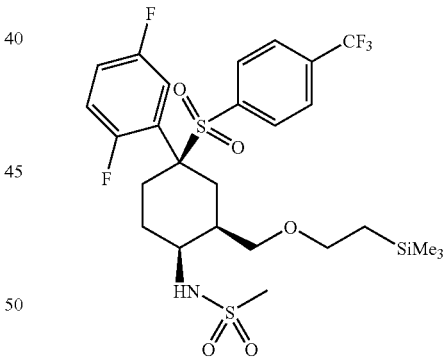

Step 1

Triethylamine (175 μL, 1.26 mmol) was added to a solution of the product of Example 15 Step 1 (230 mg, 0.419 mmol) and methanesulfonyl chloride (65 μL, 0.838 mmol) in dichloromethane (5 mL). The mixture was stirred at room temperature for 3 h., evaporated to dryness and the residue partitioned between ethyl acetate and 2 M hydrochloric acid. The organic layer was washed with 2 M hydrochloric acid, and then 4 M sodium hydroxide, dried (MgSO₄), filtered and the solvent removed to give the desired methanesulfonamide as a light yellow foam.

Step 2

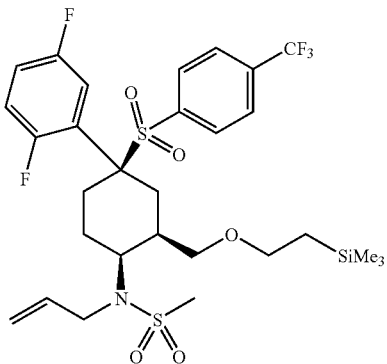

The product of Step 1 (263 mg, 0.419 mmol) in dimethylformamide (5 mL) was treated with sodium hydride (60% dispersion in mineral oil, 90 mg, 2.25 mmol), the reaction mixture was stirred at room temperature for 30 min., then allyl bromide (382 μL, 4.51 mmol) was added. The reaction mixture was then heated to 65° C. and stirred overnight. The cooled reaction mixture was quenched with water and extracted with ethyl acetate. The organic extract was washed with water, dried (MgSO₄), filtered and the solvent was removed. The residue was purified by column chromatography on silica gel eluting with 25% ethyl acetate: 75% isohexane to give the N-allyl derivative as a yellow foam. Yield 150 mg.

Step 3

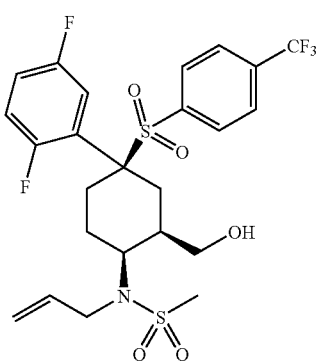

The product of Step 2 (150 mg, 0.225 mmol) was treated with boron trifluoride diethyl etherate (250 μL, 1.99 mmol) as described in Example 1 Step 3 to yield the alcohol (115 mg).

Step 4

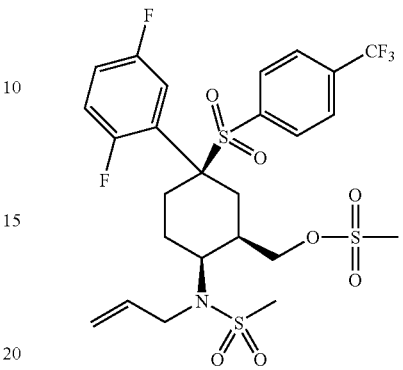

The alcohol from Step 3 (115 mg, 0, 203 mmol) and methanesulfonyl chloride (47 μL, 0.609 mmol) in dichloromethane (5 mL) were treated with triethylamine (141 μL, 1.01 mmol) and the mixture stirred at room temperature for 3 h. The solvent was removed under reduced pressure, and the residue partitioned between ethyl acetate and 2 M hydrochloric acid. The organics were collected, washed with 2 M hydrochloric acid, and then 4 M sodium hydroxide, dried (MgSO₄), filtered and the solvent was removed, azeotroping with toluene to remove all traces of ethyl acetate, to give the mesylate as a white foam. Yield 130 mg.

Step 5

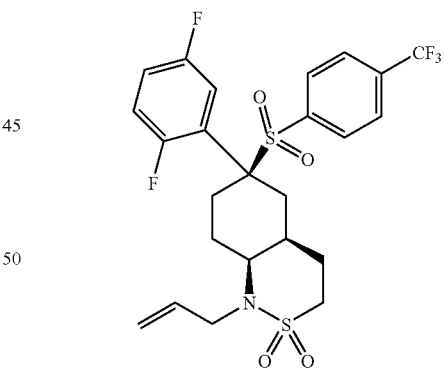

The mesylate from Step 4 (130 mg, 0.202 mmol) in tetrahydrofuran (5 mL) at −30° C. under nitrogen gas was treated with butyllithium (1.6 M solution in hexanes, 252 μL) and the reaction mixture was allowed to warm up slowly to room temperature, then quenched with water and extracted with ethyl acetate. The organic extract was washed with water, dried (MgSO₄), filtered and evaporated. The residue was purified by column chromatography on silica gel eluting with 25% ethyl acetate: 75% isohexane to give the desired cyclic sulfonamide as a white powder. Yield 15 mg (14%).

Step 6

The product of Step 5 (12 mg, 0.022 mmol) in toluene (2 mL) was treated with [1.3-bis (diphenylphosphino)propane] dichloronickel(II) (1.2 mg, 0.0022 mmol) then diisobutylaluminum hydride (1.5 M solution in toluene, 30 μL). The mixture was stirred at room temperature for 3 h., then quenched with 4 M sodium hydroxide and extracted with ethyl acetate. The organic extracts were dried (MgSO$_4$), filtered through a plug of silica gel eluting with ethyl acetate and evaporated to dryness. The residue was triturated in diethyl ether and the solid was collected to give the title compound as a white solid. Yield 6 mg (55%).

$^1$H NMR (500 MHz, CDCl$_3$) δ 7.67 (2H, d, J 8.1 Hz), 7.53 (2H, d, J 8.1 Hz), 7.12-7.07 (2H, m), 6.90-6.78 (1H, m), 4.45-4.37 (1H, m), 3.76-3.71 (1H, m), 3.20-3.11 (1H, m), 3.10-3.04 (1H, m), 2.71-2.61 (1H, m), 2.55-2.42 (2H, m), 2.40-2.29 (1H, m), 2.10-1.98 (1H, m), 1.91-1.84 (1H, m), 1.72-1.60 (2H, m), 0.98-0.91 (1H, m). m/z (ES$^-$) (M−1) 508.

Example 44

(3S,4aR,6R,8aS)-6-(2,5-difluorophenyl)-3-ethyl-6-{[14-(trifluoromethyl)phenyl]sulfonyl}octahydro-1H-2,1-benzothiazine 2,2-dioxide

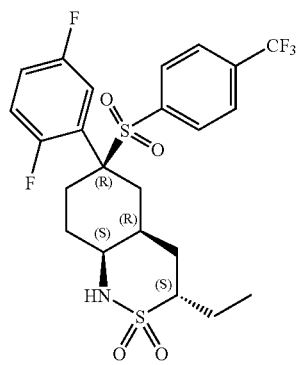

Step 1

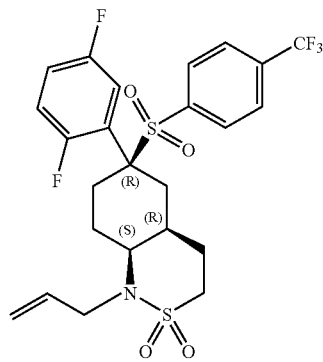

Intermediate 3 (830 mg, 1.29 mmol) was treated as described in Example 15 Step 1 and Example 43 to give the chiral N-allyl sulfonamide as a white solid. Yield 300 mg (42%).

$^1$H NMR (500 MHz, CDCl$_3$) δ 7.67 (2H, d, J 8.1 Hz), 7.53 (2H, d, J 8.1 Hz), 7.12-7.06 (2H, m), 6.88-6.77 (1H, m), 6.07-5.98 (1H, m), 5.28 (1H, dd, J 0.5 and 17.6 Hz), 5.23 (1H, dd, J 0.5 and 10.5 Hz), 4.41-4.31 (1H, m), 3.71-3.61 (1H, m), 3.28-3.20 (1H, m), 3.10-3.02 (1H, m), 2.91-2.80 (1H, m), 2.56-2.25 (5H, m), 1.98-1.90 (1H, m), 1.81-1.66 (1H, m), 1.45-1.30 (2H, m).

Step 2

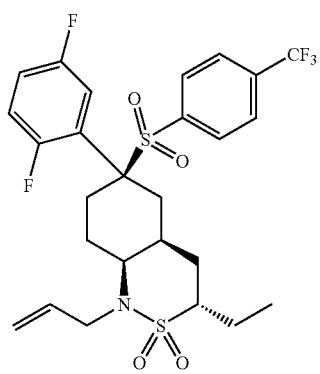

and

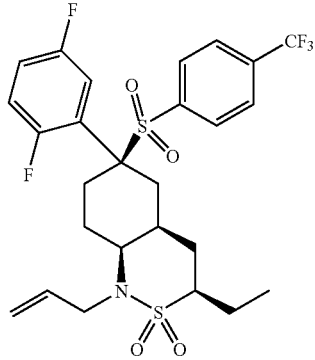

The product of Step 1 (80 mg, 0.146 mmol) in tetrahydrofuran (5 mL) at 0° C. was treated with lithium bis(trimethylsilyl)amide (1M solution in tetrahydrofuran, 292 μL) and the mixture was stirred at 0° C. for 30 min. before addition of iodoethane (15 μL, 0.188 mmol). The resulting mixture was allowed to warm up slowly overnight, quenched with water then extracted with ethyl acetate. The organic extracts were dried (MgSO$_4$), filtered and the solvent was removed. The residue was purified by column chromatography on silica gel eluting with 10 to 15% ethyl acetate: isohexane to give a less polar product (white solid, yield 28 mg, 33%):

¹H NMR (500 MHz, CD₃OH) δ 7.81 (2H, d, J 8.3 Hz), 7.66 (2H, d, J 8.3 Hz), 7.24-7.14 (2H, m), 7.02-6.93 (1H, m), 6.04-5.93 (1H, m), 5.32 (1H, d, J 17.2 Hz), 5.19 (1H, d, J 10.1 Hz), 4.26 (1H, dd, J 5.1 & 17.2 Hz), 3.77 (1H, dd, J 7.0 & 17.2 Hz), 3.54 (1H, brs), 3.16-3.11 (1H, m), 2.83-2.68 (1H, m), 2.61-2.39 (2H, m), 2.33-2.02 (2H, m), 2.08-1.85 (2H, m), 1.55-1.28 (3H, m), 1.11-0.98 (3H, m), 0.93-0.82 (1H, m); and also a more polar product (white solid, yield 23 mg 27%):

¹H NMR (500 MHz, CD₃OH) δ 7.83 (2H, d, J 8.3 Hz), 7.66 (2H, d, J 8.3 Hz), 7.24-714 (2H, m), 7.04-6.94 (1H, m), 5.92-5.81 (1H, m), 5.24 (1H, dd, J 1.1 & 17.2 Hz), 5.13 (1H, dd, J 1.1 & 10.3 Hz), 4.13-4.05 (1H, dd, m), 3.75 (1H, dd, J 6.8 & 16,7 Hz), 3.59-3.53 (1H, m), 3.00-2.93 (1H, m), 2.70-2.55 (2H, m), 2.48-2.22 (4H, m), 2.13-2.03 (1H, m), 1.93-1.85 (1H, m), 1.75-1.66 (1H, m), 1.59-1.47 (1H, m), 1.17-1.07 (3H, m), 0.95-0.84 (1H, m).

Step 3

The less polar product from Step 2 (25 mg, 0.0433 mmol) was treated as described in Example 43 Step 6 to give the desired chiral sulfonamide as a white solid. Yield 20 mg (86%).

¹H NMR (500 MHz, CD₃OH) δ 7.82 (2H, d, J 8.2 Hz), 7.64 (2H, d, J 8.2 Hz), 7.23-708 (2H, m), 7.01-6.93 (1H, m), 3.57-3.52 (1H, m), 3.06-2.98 (1H, m), 2.75-2.56 (2H, m), 2.51-2.37 (2H, m), 2.00-1.91 (2H, m), 1.90-1.82 (1H, m), 1.74-1.55 (2m H, m), 1.51-1.42 (1H, m), 1.23-1.20 (1H, m), 1.15-1.07 (3H, m), 0.97-0.84 (1H, m), m/z (ES⁻) (M-1) 536.

Example 45

(3R,4aR,6R,8aS)-6-(2,5-difluorophenyl)-3-ethyl-6-([4-(trifluoromethyl)phenyl]sulfonyl}octahydro-1H-2,1-benzothiazine 2,2-dioxide

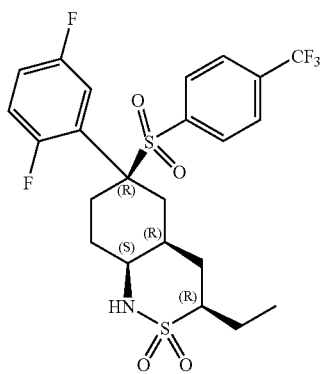

The more polar isomer from Example 44 Step 2 (23 mg, 0.0433 mmol) was treated as described in Example 43 Step 6 to give the desired chiral sulfonamide as a white solid. Yield 10 mg (46%).

¹H NMR (500 MHz, CD₃OH) δ 7.84 (2H, d, J 8.2 Hz), 7.65 (2H, d, J 8.2 Hz), 7.27-7.08 (2H, m), 7.04-6.94 (1H, m), 3.62-3.57 (1H, m), 2.93-2.86 (1H, m), 2.75-2.63 (1H, m), 2.56-2.49 (2H, m), 2.48-2.41 (1H, m), 2.40-2.32 (1H, m), 2.17-2.07 (1H, m), 2.00-1.93 (1H, m), 1.91-1.84 (1H, m), 1.79-1.70 (1H, m), 1.68-1.55 (1H, m), 1.32-1.25 (1H, m), 1.20-1.14 (3H, m), 0.98-0.85 (1H, m). m/z (ES-) (M-1) 536.

Example 46

(3RS,4aRS,6RS,8aSR)-6-(2,5-difluorophenyl)-3-isopropyl-6-{[[4-(trifluoromethyl)phenyl]sulfonyl}octahydro-1H-2,1-benzothiazine 2,2-dioxide

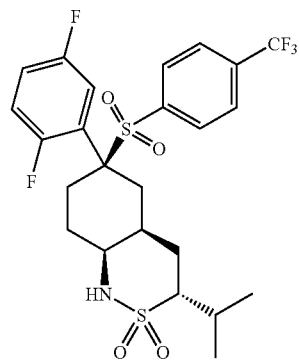

Step 1

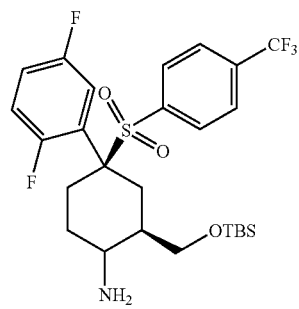

The product from Example 15 Step 2 (2 g, 3.1 mmol) in dichloromethane (25 mL) was treated with triethylamine (1.7 mL, 12.4 mmol), 4-dimethylaminopyridine (cat.) and ᵗbutyldimethylsilyl chloride (1.16 g, 7.75 mmol). After 16 hours the mixture was washed with 10% citric acid (10 mL), sodium bicarbonate (sat., 20 mL) and brine (sat. 15 mL). The organics were dried (MgSO₄) and evaporated and the residue was filtered through silica eluting with 1% ammonia in ethyl acetate to give the desired t-butyldimethylsilyl ether as a white solid (1.8 g) MS ES+564.

Step 2

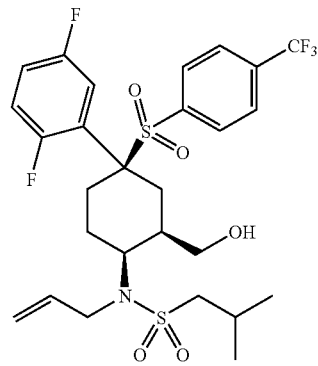

The silyl ether from Step 1 (1.8 g, 3.2 mmol) and isobutanesulfonyl chloride (1.12 g, 8 mmol) were stirred in dichloromethane (20 mL) and triethylamine (1.34 mL, 9.5 mmol) was added. After stirring at room temperature for 16 h., the mixture was evaporated to dryness and the residue was partitioned between ethyl acetate and 2 M hydrochloric acid. The organic layer was collected, washed with 2 M hydrochloric acid and then 4 M sodium hydroxide, dried (MgSO$_4$), filtered and the solvent removed in vacuo. The residue was purified by column chromatography (eluting with 20% ethyl acetate in hexanes) to give the sulphonamide (900 mg). This product was dissolved in dimethylformamide (6 mL) and sodium hydride (60% dispersion in mineral oil, 132 mg, 3.3 mmol) was added. The mixture was stirred at room temperature for 30 min., allyl bromide (1.1 mL, 13 mmol) was added, then the mixture was heated to 65° C. over 72 hrs. After cooling to room temperature and quenching with water, the mixture was extracted with ethyl acetate. The organic extract was washed with water, dried (MgSO$_4$), filtered and the solvent was removed. The residue was purified by column chromatography on silica gel eluting with 20% ethyl acetate: 80% isohexane to give the N-allyl derivative (400 mg).

Step 3

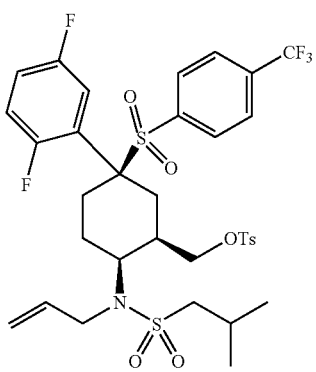

Prepared from the product of Step 2 (0.2 g) and p-toluenesulfonyl chloride by the procedure of Example 32 Step 4. Purified by column chromatography on silica, eluting with 30% ethyl acetate in hexanes to give the tosylate (185 mg).

Step 4

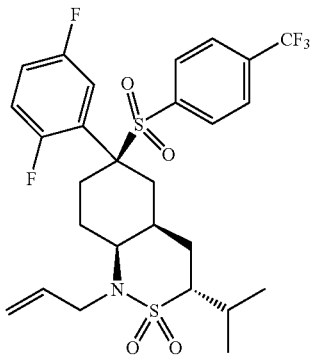

and

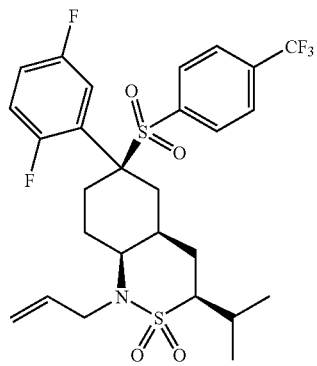

The tosylate from Step 3 (186 mg, 0.24 mmol) in tetrahydrofuran (9 mL) at 40° C. under nitrogen was treated with lithium hexamethyldisilazide (1.0 M solution in tetrahydrofuran, 480 μL) and the reaction mixture was allowed to warm up slowly to room temperature, then quenched with saturated aqueous ammonium chloride and extracted with ethyl acetate. The organic extract was washed with water, dried (MgSO$_4$), filtered and the solvent was removed. The residue was purified by column chromatography on silica gel eluting with 15% ethyl acetate: 85% iso-hexane. to give a less polar product as a white solid (48 mg):

$^1$H NMR (500 MHz, CDCl$_3$) δ 7.66 (2H, d, J 8Hz), 7.52 (2H, d, J 8 Hz), 7.11-7.07 (1H, m), 6.93-6.75 (2H, m), 6.06-5.96 (1H, m), 5.29-5.22 (2H, m), 4.41-4.33 (1H, m), 3.69-3.48 (2H, m), 3.07-2.99 (1H, m), 2.89-2.72 (1H, m), 2.61-2.20 (5 H, m), 1.90-1.73 (2H, m), 1.48-1.30 (2H, m), 1.17 (3H, d, J=7 Hz) and 1.05 (3H, d, J=7Hz); and also a more polar product as a white solid. (67 mg):

$^1$H NMR (500 MHz, CDCl$_3$) δ 7.65 (2H, d, J 8Hz), 7.54 (2H, d, J 8 Hz), 7.07-7.07 (2H, m), 6.86-6.78 (1H, m), 5.75-5.65 (1H, m), 5.04-4.99 (2H, m), 3.95 (1H, dd, J=and 4.5 Hz), 3.63 (1H, dd, J=15.5 and 6.5 Hz), 3.29-3.24 (1H, m), 2.76-2.72 (1H, m), 2.61-2.52 (4H, m), 2.49-2.42 (1H, m), 2.40-2.18 (3H, m), 2.09-2.00 (1H, m), 1.75-1.68 (1H, m), 1.17 (3H, d, J=6.8 Hz) and 1.09 (3H, d, J=6.8 Hz).

Step 5

The less polar product from Step 4 (40 mg, 0.067 mmol) was treated as described in Example 43 Step 6 to give the title compound as a white solid. 23 mg . $^1$H NMR (500 MHz, CDCl$_3$) δ 7.67 (2H, d, J 8.3 Hz), 7.53 (2H, d, J 8.0 Hz), 7.25-6.88 (2H, m), 7.11-7.06 (1H, m), 4.68-4.50 (1H, brs), 3.69-3.68 (1H, m), 3.00-2.96 (1H, m), 2.71-2.65 (1H, m), 2.60-2.27 (3H, m), 2.18-2.13 (1H, m), 2.02-1.87 (2H, m), 1.80-1.52 (3H, m), 1.22 (3H, d, J 6.9 Hz), 1.07 (3H, d, J 6.9 Hz). m/z (ES$^-$) (M−1) 550.

Example 47

(3SR,4aRS,6RS,8aSR)-6-(2,5-difluorophenyl)-3-isopropyl-6-{[4-(trifluoromethyl)phenyl]sulfonyl}octahydro-]H-2,1-benzothiazine 2,2-dioxide

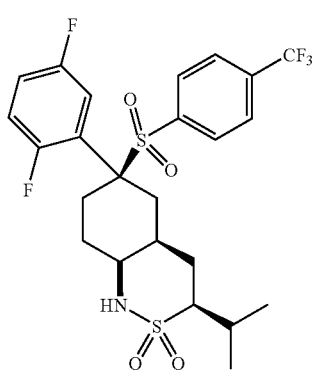

Step 5 of Example 46 was repeated, using the more polar isomer from Step 4 (40 mg, 0.067 mmol) to give the title compound as a white solid. (23 mg). ¹H NMR (500 MHz, CDCl₃) δ 7.68 (2H, d, J 8.3 Hz), 7.54 (2H, d, J 8.2 Hz), 7.10-7.06 (2H, m), 6.87-6.82 (1H, m), 4.47 (1H, d, J 8.9 Hz), 3.60-3.57 (1H, m), 2.82-2.77 (1H, m), 2.71-2.52 (2H, m), 2.40-2.20 (4H, m), 1.98 (1H, dd, J=15.1 and 2 Hz), 1.81-1.77 (2H, m), 1.76-1.74 (1H, m), 1.26 (3H, d, J 6.4 Hz), 1.11 (3H, d, J 6.8 Hz). m/z (ES⁻) (M−1) 550.

Example 48

(4aRS,6RS,8aSR)-6-[(4-chlorophenyl)sulfonyl]-6-(2,5-difluorophenyl)octahydro-1H-isothiochromene 2,2-dioxide

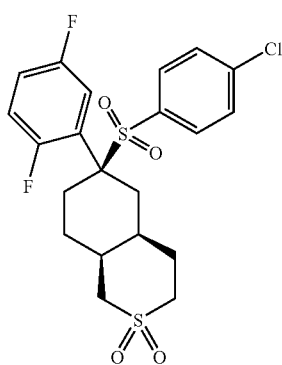

Step 1

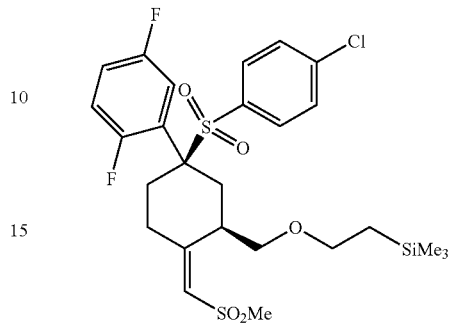

Diethyl (methylsulphonylmethyl)phosphonate [*J. Org. Chem.* 1972, 37(22), 3547-9] (0.49 g, 2.1 mmol) in dry tetrahydrofuran (10 mL) was treated dropwise with 1.0 M butyl lithium (1.25 mL, 2 mmol) at −78° C. The mixture was allowed to warm to −50° C. over 1 hour before adding Intermediate 1 (1.0 g, 1.9 mmol), then allowing the mixture to warm to r.t. over 16 hours. The mixture was diluted with ethyl acetate (10 mL), washed with water (10 mL), and the organic phase separated, dried (Na₂SO₄) and evaporated to dryness. The residue was purified on silica eluting with [7:3] hexane-ethyl acetate to give the vinyl sulfone (0.7 g).

Step 2

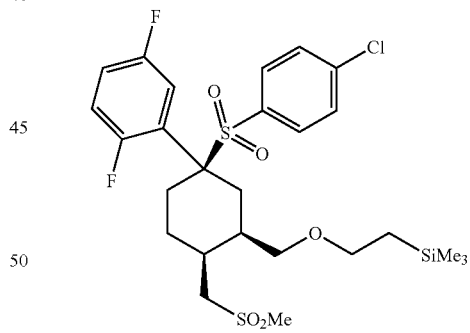

The product from Step 1 (0.7 g, 1.2 mmol) in dry tetrahydrofuran (90 mL) was treated dropwise with 1.0 M L-Selectride (1.8 mL, 1.8 mmol) at −40° C. The mixture was held at this temperature for 2 hours and then allowed to warm to 0C over 1 hour before adding ethanol (3 drops). The reaction mixture was diluted with ethyl acetate (10 mL), washed with water (10 mL), and the organic phase washed with brine (sat), separated, dried (Na₂SO₄) and evaporated to dryness. The residue was purified on silica eluting with [3:1] hexane-ethyl acetate to give the desired product (0.7 g). ¹H NMR CDCl₃ 7.35-7.28 (4H, m), 7.11-6.79 (2H, m), 7.06-7.02 (1H, m), 3.47-3.11 (6H, m), 2.92 (3H, s), 2.70-2.20 (5H, m), 1.97-1.79 (2H, m), 1.49-1.38 (1H, m), 0.91-0.84 (2H, m) and 0.03 (9H, s).

Step 3

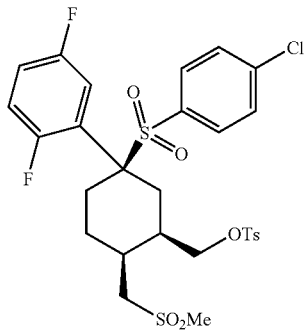

Prepared from the product of Step 2 by treatment with BF$_3$ etherate, following the procedure of Example 1 Step 3, then tosylation by the procedure of Example 32 Step 4. Yield 0.425 g Step 4

The procedure of Example 43 Step 5 was followed, using the tosylate from Step 3 (106 mg, 0.16 mmol), to give the desired cyclic sulfone (75 mg).

$^1$H NMR (500 MHz, CDCl$_3$) δ 7.38 (2H, d, J 8.7 Hz), 7.30 (2H, d, J 8.5 Hz), 7.15-6.80 (2H, m), 7.09-7.06 (1H, m), 3.37 (1H, t, J=14 Hz), 3.08-3.02 (1H, m), 2.96-2.90 (1H, m), 2.80 (1H, dt, J=14.5 and 3.5 Hz), 2.70-2.15 (6H, m), 2.02-1.93 (1H, m), and 1.87-1.62 (3H, m).

Example 49

(4aRS,6RS,8aSR)-6-(2,5-difluorophenyl)-2,2-dioxidooctahydro-1H-isothiochromen-6-yl 4-(trifluoromethyl)phenyl sulfone

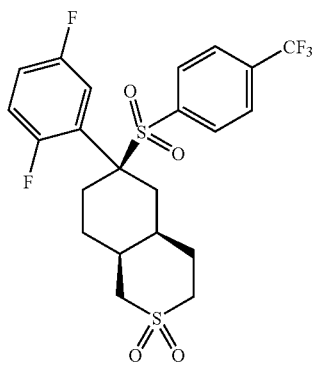

Prepared as described for Example 48, substituting Intermediate 2 for Intermediate 1 in the initial step.

$^1$H NMR (500 MHz, CDCl$_3$) δ 7.66 (2H, d, J 8.2 Hz), 7.51 (2H, d, J 8.2 Hz), 7.25-6.78 (2H, m), 7.10-7.07 (1H, m), 3.38 (1H, t, J=13.9 Hz), 3.08-3.02 (1H, m), 2.96-2.90 (1H, m), 2.80 (1H, dt, J=14.5 and 3.5 Hz), 2.70-2.19 (6H, m), 2.02-1.93 (1H, m), and 1.87-1.62 (3H, m).

Example 50

(3SR,4aRS,6RS,8aSR)-6-[(4-chlorophenyl)sulfonyl]-6-(2,5-difluorophenyl)-3-ethyloctahydro-1H-isothiochromene 2,2-dioxide

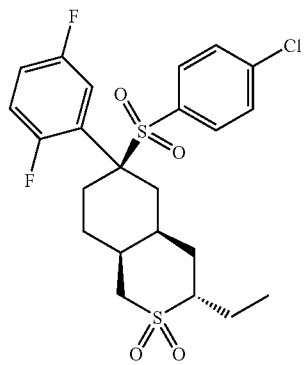

Prepared as described in Example 48, substituting diethyl (propanesulfonylmethyl)phosphonate for diethyl (methanesulfonylmethyl)phosphonate in Step 1.

$^1$H NMR (500 MHz, CDCl$_3$) δ 7.39-7.37 (2H, m), 7.31-7.29 (2H, m), 7.22-6.78 (2H, m), 7.09-7.05 (1H, m), 3.37 (1H, t, J=13.9 Hz), 2.86-2.82 (1H, m), 2.80 (1H, dd, J=14.3 and 3.7 Hz), 2.68-2.13 (6H, m), 2.02-1.49 (6H, m), and 1.11 (3H, t, J=7.5 Hz).

Example 51

(3S,4aR,6R,8aS)-6-[(4-chlorophenyl)sulfonyl]-6-(2,5-difluorophenyl)-3-ethyloctahydro-1H-2,1-benzothiazine 2,2-dioxide

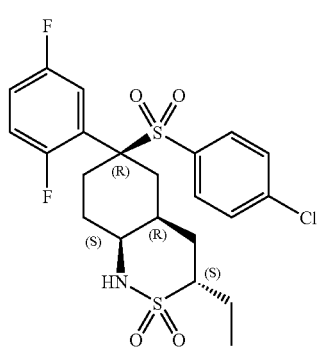

Step 1

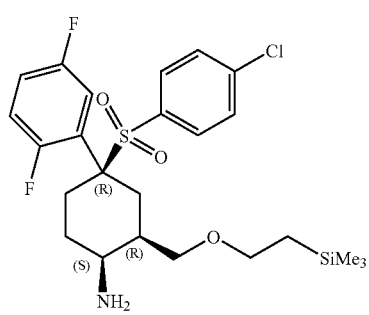

Intermediate 4 was treated as described in Example 1 Steps 1 and 2. The resulting product (80% e.e) (3.6 g, 6.96 mmol) was dissolved in iso-propanol (34 mL) and (1S)-(+)-camphor sulfonic acid (1.37 g, 5.91 mmol) was added. The mixture was heated to reflux, allowed to cool to room temperature slowly, and then left in the refrigerator overnight. The resulting solid was collected, washed with pre-cooled (−5° C.) isopropanol, then suspended in ethyl acetate and washed with 4M sodium hydroxide. The organics were dried (MgSO$_4$), filtered and the solvent removed to give the chiral amine (98% e.e). Yield 3 g, NMR data identical to those observed for the product of Example 1 Step 2.

Step 2

The amine from Step 1 (3 g) was elaborated as described for Example 43 Steps 1-5 to provide the desired homochiral sulfonamide (60 mg).

$^1$H NMR (500 MHz, CD$_3$OH) δ 7.51 (2H, d, J 8.7 Hz), 7.40 (2H, d, J 7.9 Hz), 7.25-7.11 (2H, m), 7.04-6.94 (1H, m), 3.55-3.51 (1H, m), 3.03-2.97 (1H, m), 2.75-2.32 (4H, m), 2.17-2.07 (1H, m), 2.01-1.93 (2H, m), 1.91-1.84 (1H, m), 1.75-1.57 (2H, m), 1.50-1.44 (1H, m) and 1.11 (3H, t,J 7.6 Hz).

Example 52

(4aRS,6RS,8aSR)-3-cyclopropyl-6-(2,5-difluorophenyl)-6-{[4-(trifluoromethyl)phenyl]sulfonyl}octahydro-1H-2,3-benzothiazine 2,2-dioxide

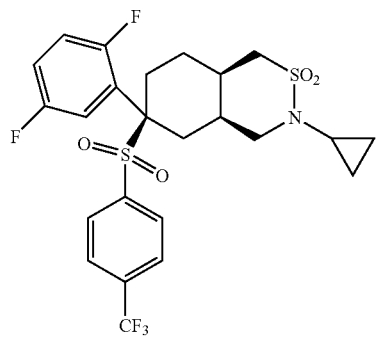

Step 1

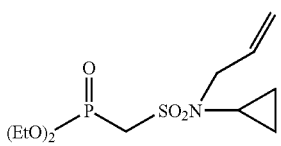

The methanesulfonyl derivative of cyclopropylamine was N-alkylated with allyl bromide by the procedure described in Example 43 Step 2. The resulting product (3.6 g, 0.021 moles) in THF (40 mL) at −78° C. under a nitrogen atmosphere was treated with a 1.6 M solution of butyl lithium in hexanes (14.1 mL, 0.023 moles). After 20 minutes, diethylchlorophosphonate (3.9 g, 0.023 moles) was added and stirring continued for 2 hr. The reaction was quenched (water), extracted (ethyl acetate), and the extracts washed (water, brine), dried (magnesium sulphate) and evaporated in vacuo. Purification by flash silica chromatography, using 40% ethyl acetate/isohexane to elute, gave the desired product (2.9 g, 44% yield).

Step 2

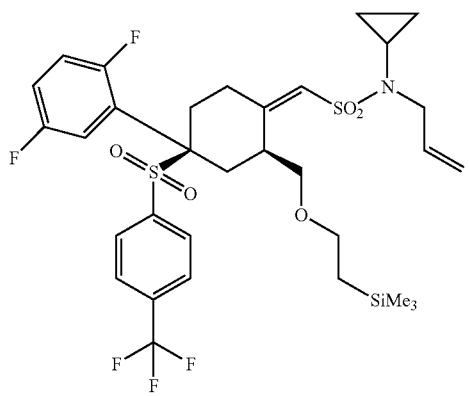

The product of Step 1 (1.0 g, 3.2 mmoles) in THF (10 μL) at −78° C. under a nitrogen atmosphere was treated with butyl lithium (1.6M in hexanes, 2.2 mL, 3.5 mmoles), then aged for 10 minutes before addition of Intermediate 2 (1.76 g, 3.2 mmoles) in THF (10 mL). After stirring for 16 h., the reaction was quenched with water, extracted into ether, washed (brine), dried (magnesium sulphate) and evaporated in vacuo. The residue was purified by flash silica chromatography, using 10-20% ethyl acetate/isohexane to elute, giving the vinyl sulfonamide, 0.6 g, 27% yield.

Step 3

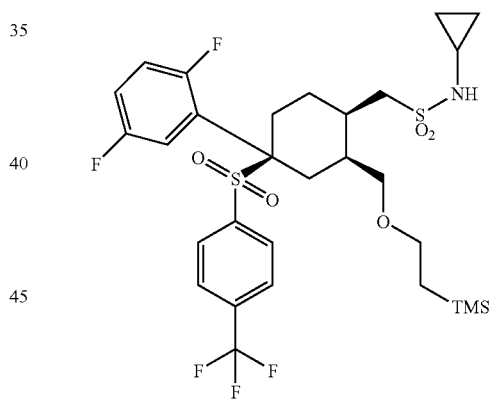

The product of Step 2 (0.4 g, 0.56 mmoles) in methanol (10 mL) at 0° C. under N$_2$ was treated with nickel (II) chloride (0.02 g, 0.112 mmoles) followed by portionwise addition of sodium borohydride (0.22 g, 5.6 mmoles). After 3 hours, the reaction mixture was filtered and evaporated in vacuo, and the residue partitioned between ethyl acetate and water. The organic layer was washed (brine), dried (magnesium sulphate) and evaporated in vacuo. Purification of the residue by flash silica chromatography, using 20% ethyl acetate/iso-hexane to elute, gave the desired product. (0.031 g, 8% yield).

Step 4

The product of Step 3 was treated with BF$_3$ etherate by the procedure of Example 1 Step 3. The resulting alcohol (0.042 g, 0.079 mmoles) in dichloromethane (0.6 mL) at 0° C. was treated with triethylamine (0.012 g, 0.12 mmoles) in dichloromethane (0.2 mL) followed by methanesulfonyl chloride (0.011 g, 0.095 mmoles) in dichloromethane (0.2 mL). The mixture was stirred for 60 minutes, diluted with dichloromethane (2 mL), washed (water, brine), dried (magnesium sulphate), passed through a plug of silica (eluting with ethyl acetate) and evaporated in vacuo. The resulting crude mesylate in N,N-dimethylformamide (1.0 mL) under nitrogen at 0° C. was treated with a 60% dispersion of sodium hydride in mineral oil (0.004 mg, 0.093 mmoles) and stirred for 60 minutes. The reaction was quenched (0.5 M citric acid solution), extracted into ethyl acetate, washed (water, brine), dried (magnesium sulphate), and evaporated in vacuo. Purification of the residue by flash silica chromatography, using ethyl acetate/isohexane mixtures to elute, gave the desired cyclic sulfonamide, 0.006 g, 18% yield.

$^1$H NMR (400 MHz, CDCl$_3$) δ 0.45 (1H, vbrs), 0.70-0.78 (1H, m), 0.85-0.96 (1H, m), 1.08-1.15 (1H, m), 1.60-1.75 (2H, m), 2.14-2.61 (7H, m), 2.83-3.06 (1H, m), 3.04-3.39 (1H, m), 3.32-3.39 (1H, m), 3.59-3.63 (1H, m), 6.84 (1H, vbrs), 7.06-7.12 (2H, m), 7.50 (2H, d, J=8.2 Hz), 7.67 (2H, d, J=8.2 Hz). MS (ES$^+$) MH$^+$=550.

Example 53

(4aSR,6RS,8aSR)-3-cyclopropyl-6-(2,5-difluorophenyl)-6-{[6-(trifluoromethyl)pyridin-3-yl]sulfonyl}octahydro-1H-2,1,3-benzothiadiazine 2,2-dioxide

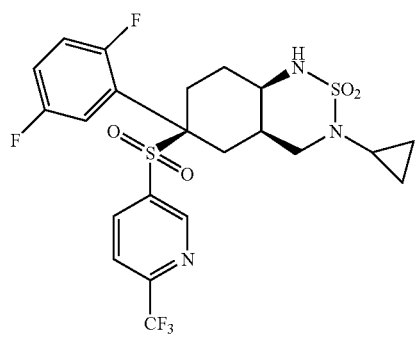

Prepared from Intermediate 5 (100 mg, 0.17 mmol) using the procedure detailed for Example 4. Yield 69 mg (71%).

$^1$H NMR (360 MHz, CDCl$_3$) δ 0.39-0.50 (1H, m), 0.65-0.74 (1H, m), 0.71-0.93 (3H, m), 1.58-1.75 (2H, m), 1.98 (1H, bd, J=14.4 Hz), 2.14-2.22 (1H, m), 2.26-2.33 (1H, m), 2.45-2.70 (2H, m), 3.04-3.15 (1H, m), 3.55 (1H, bd, J=14.4 Hz), 3.84 (1H, bd, J=14.4 Hz), 4.45 (1H, d, J=10.8 Hz), 6.78-6.92 (1H, m), 7.10-7.20 (2H, m), 7.74 (1H d, J=8.3 Hz), 7.84-7.90 (1H, m), 8.60 (1H, bs).

Example 54

(4aS,6R,8aS)-3-cyclopropyl-6-(2,5-difluorophenyl)-6-{[6-(trifluoromethyl)pyridin-3-yl]sulfonyl}octahydro-1H-2,1,3-benzothiadiazine 2,2-dioxide

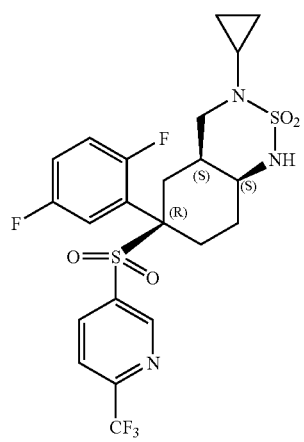

The product of Example 53 was separated into its constituent enantiomers by chiral HPLC (Chiralpak AD, column dimensions 250×21.0 mm i.d.). The racemate (70 mg) was dissolved in 2 mL ethanol, and using 50 μl injections, column loadings of 1.75 mg were achieved eluting with 30% ethanol in isohexanes The second eluting peak was Example 54 (12 mg) and NMR data were identical to those specified for Example 53.

Example 55

(3S,4aR,6R,8aS)-6-(2,5-difluorophenyl)-3-ethyl-6-{[4-(trifluoromethyl) phenyl]sulfonyl}octahydro-1H-2,1-benzothiazine 2,2-dioxide

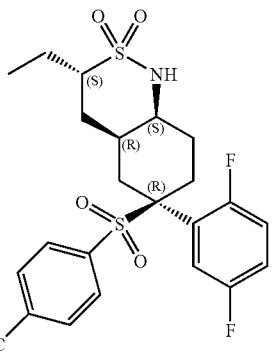

alternative route.

Step 1

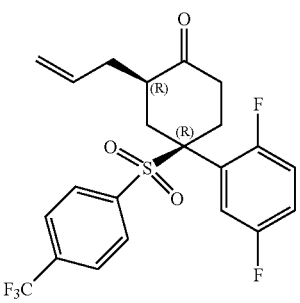

A solution of (1 S)-1-phenyl-N-[(1 S)-1-phenylethyl] ethanamine (10.8 g, 47.85 mmol) and oven-dried lithium chloride (3.0 g, 71.80 mmol) in tetrahydrofuran (200 ml) was degassed under nitrogen. The reaction mixture was cooled to −78° C. (internal temperature) and treated with n-butyl lithium (1.6M in hexane, 30 ml, 47.85 mmol), dropwise over 25 minutes. After the addition, the reaction was warmed to −20° C. and then cooled to −100° C. and stirred for 2 hours. A solution of 4-(2,5-difluorophenyl)-4-[[4-(trifluoromethly)pheny]sulfonyl]-cycolhexanone (20 g, 47.85 mmol) in tetrahydrofuran (100 ml) (cooled to −78° C.) was cannulated into the reaction vessel over 20 minutes. After a further 30 minutes at −100° C., allyl iodide (8.80 ml, 95.60 mmol) was added and the reaction mixture was allowed to warm to room temperature over 18 hours. The reaction mixture was acidified with citric acid solution (200 ml) and diluted with ethyl actetate (300 ml). The ethyl acetate layer was separated and re-washed with citric acid solution (200 ml), 10% ammonia solution (200 ml), brine, dried over MgSO₄, filtered and evaporated in vacuo. Purification by column chromatography gave the title compound as a white solid (8.97 g, 41%, 70% ee). A solution of this material (73.1 g, 61% ee) in toluene (181 ml) was added dropwise to isohexane (760 ml) stirring at 70° C., over 45 minutes. The reaction mixture was seeded with racemic product (100 mg) and was cooled slowly over 2½ hours. The resultant solid was filtered and the filtrate was evaporated in vacuo resulting in clear gummy oil (49 g, 95% ee).

Step 2

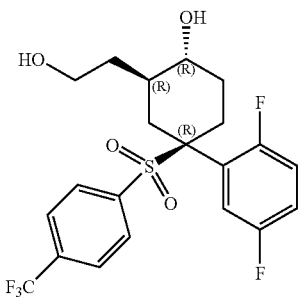

Oxygen was bubbled through a stirred solution of the product of Step 1 (67.8 g, 148 mmol) in dichloromethane (750 ml) and methanol (150 ml) at −78° C. for 10 minutes. Ozone was bubbled into the reaction mixture until a blue coloration persisted (3 ½ hours), followed by oxygen and then nitrogen until the blue color disappeared. Sodium borohydride (14 g, 370 mmol) was added to the reaction mixture, which was then allowed to warm to room temperature slowly. The mixture was acidified with citric acid solution (200 ml) and 2N hydrochloric acid, until pH 2, and diluted with dichloromethane (800 ml). The dichloromethane layer was separated and washed with water, brine, dried over MgSO₄, filtered and evaporated in vacuo. Purification by recrystallization from ether and isohexane (50:50), gave the diol as a white solid (50 g, 73%, 97% ee).

Step 3

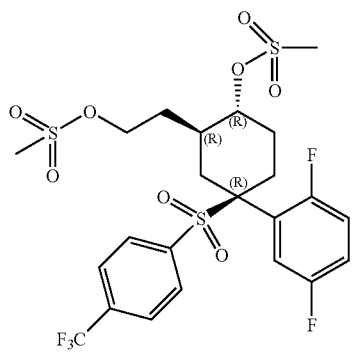

Methanesulfonyl chloride (20 ml, 259 mmol) was added slowly to a solution of the product of Step 2 (50 g, 108 mmol) in dichloromethane (700 ml) and triethylamine (45 ml, 324 mmol), stirring at −10° C. The reaction mixture was allowed to stir at −10° C. for 2 hours. The reaction was acidified with citric acid solution (500 ml) and diluted with dichloromethane (500 ml). The dichloromethane layer was separated and washed with sodium hydrogen carbonate solution (500 ml), brine, dried over MgSO₄, filtered and evaporated in vacuo to give the bis-mesylate as white foam (67.7 g, >100%), which was used without further purification.

Step 4

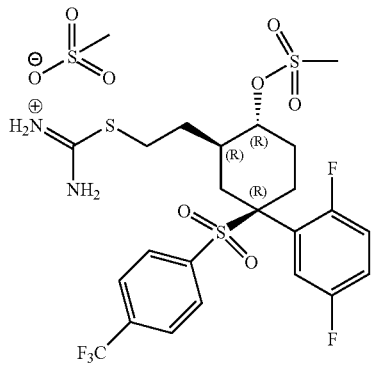

A solution of the product of Step 3 (67.7 g, 109 mmol) in ethanol was treated with thiourea (8.7 g, 115 mmol). The reaction mixture was stirred at 80° C. for 18 hours, cooled to room temperature and evaporated in vacuo to give the desired product as pale yellow foam (80.6 g, >100%).

Step 5

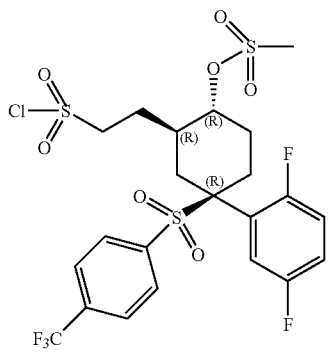

Acetic acid (500 ml) was added to a solution of the product of Step 4 (80.7 g) in water (100 ml) at room temperature. Chlorine gas (approximately 55 g) was bubbled through the reaction mixture for 30 minutes, until the reaction mixture turned a dark yellow. The reaction mixture was diluted with diethyl ether (1000 ml) and water (1000 ml). The ether layer was separated and washed with a further portion of water (1000 ml), sodium sulfite solution (500 ml), sodium hydrogen carbonate solution (3×500 ml), brine, dried over MgSO$_4$, filtered and evaporated in vacuo to give the sulfonyl chloride as a white foam 65.7 g (>100%).

Step 6

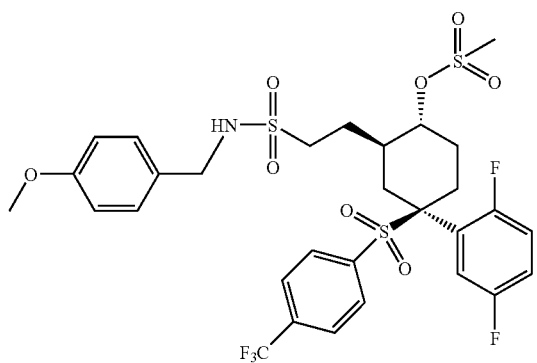

4-Methoxybenzylamine (35 ml, 263 mmol) was added dropwise over 10 minutes to a solution of the product of Step 5 (65.7 g, 105 mmol in dichloromethane (500 ml) stirred at 0° C., under nitrogen. The reaction mixture was warmed to room temperature over 90 minutes, diluted with dichloromethane (500 ml) and acidified with citric acid solution (500 ml). The dichloromethane layer was separated and washed with brine, water (700 ml), dried over MgSO$_4$, filtered and evaporated in vacuo. Purification by column chromatography gave the title intermediate as a pale brown foam (59.3 g, 88% over 4 steps).

Step 7

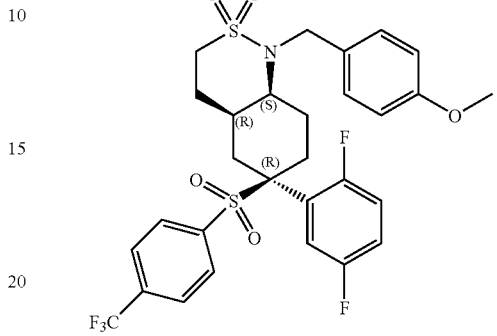

Sodium hydride (4.90 g, 127 mmol) was added to a solution of the product of Step 6 (59.3 g, 82 mmol) dissolved in dimethylformamide (700 ml). After stirring at room temperature for 10 minutes the reaction mixture was heated to 75° C. After 2 hours the reaction mixture was cooled to room temperature, acidified with citric acid solution (500 ml) and diluted with ethyl acetate (800 ml). The ethyl acetate layer was separated, washed with water (3×500 ml), brine, dried over MgSO$_4$, filtered and evaporated in vacuo. Purification by column chromatography gave the cyclised intermediate as white solid (28.7 g, 56%).

Step 8

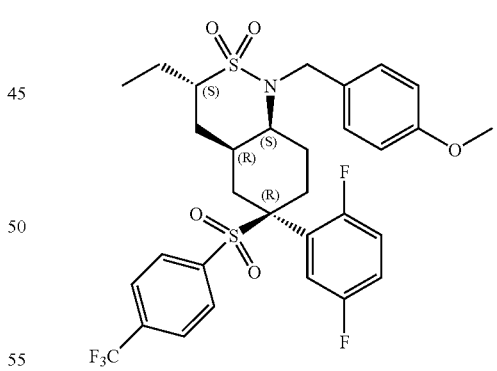

Lithium bis(trimethylsilyl)amide (1M in THF, 114 ml, 114 mmol) was added dropwise to a solution the product of Step 7 (28.7 g, 45.5 mmol) in tetrahydrofuran (300 ml) stirring at −2° C. (internal temperature). The reaction mixture was stirred for 1 hour at 0° C. under nitrogen, then cooled to −78° C. and treated with ethyl iodide (4.7 ml, 59.2 mmol). The reaction mixture was stirred at −25° C. for 18 hours then warmed to −8° C. and then to room temperature over 2 hours.

The reaction was diluted with ethyl acetate (500 ml), water (500 ml) and acidified with citric acid solution (500 ml). The ethyl acetate layer separated and the aqueous layer was extracted with ethyl acetate (3×500 ml). The organics combined, washed with brine, dried over MgSO$_4$, filtered and evaporated in vacuo. Purification by column chromatography gave the alkylated intermediate as a white foam (23.1 g, 77%).

Step 9: (3S,4aR,6R,8aS)-6-(2,5-difluorophenyl)-3-ethyl-6-{[4-(trifluoromethyl)phenyl]sulfonyl}octahydro-1H-2 1-benzothiazine 2,2-dioxide A solution of the product of Step 8 (23.1 g) in dichloromethane (115 ml) was treated with trifluoroacetic acid (60 ml) dropwise over 5 minutes, and stirred at room temperature under nitrogen for 30 minutes. The reaction mixture was evaporated in vacuo and purified by column chromatography gave the title product as white foam (17 g, 90%, 98.5% ee).

The white foam (17 g, 98.5% ee) was dissolved in ethyl acetate (34 ml) and heated to 70° C. Heptane (136 ml) was added portionwise to the stirred solution under nitrogen. After 2 hours the reaction solution was seeded with a homochiral sample of the title compound and allowed to stir for a further 1 hour and then cooled to room temperature. The resulting white solid was collected by filtration (12 g, 99.5% ee).

$^1$H NMR δ (ppm)(CDCl$_3$): 7.67 (2H, d, J=8.3 Hz), 7.56 (2H, s), 7.11-7.07 (1H, m), 6.98-6.83 (2H, m), 4.71-4.58 (1H, m), 3.68 (1H, s), 3.12 (1H, q, J=9.8 Hz), 2.73 (1 H, t, J=13.5 Hz), 2.54-2.40 (3H, m), 2.17-1.91 (4H, m), 1.65-1.48 (3H, m), 1.14 (3 H, t, J=7.5 Hz).

Example 56

(3S,4aR,6R,8aS)-6-(2,5-difluorophenyl)-3-(2-propenyl)-6-{[4-(trifluoromethyl)phenyl]sulfonyl}-octahydro-1H-2,1-benzothiazine 2,2-dioxide

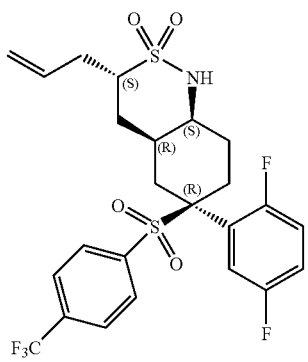

Prepared by the method of Example 55, substituting allyl iodide for ethyl iodide in Step 8.

$^1$H NMR δ (ppm)(CDCl$_3$): 7.72-7.58 (4H, m), 7.20-6.75 (3H, m), 5.90-5.80 (1H, m), 5.37-5.16 (3H, m), 3.70 (1H, s), 3.37 (1H, s), 2.90-2.70 (2H, m), 2.54-2.40 (3H, m), 2.33-2.15 (1H, m), 2.00-1.94 (3H, m), 1.80-1.52 (2H, m).

Example 57

(3R,4aR,6R,8aS)-6-(2,5-difluorophenyl)-3-(2-hydroxyethyl)-6-{[4-(trifluoromethyl)phenyl]sulfonyl}-octahydro-1H-2,1-benzothiazine 2,2-dioxide

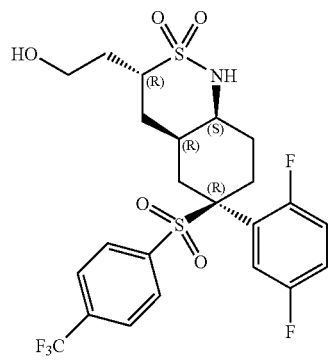

Prepared from the product of Example 56 by treatment with ozone followed by sodium borohydride using the procedure described in Example 55 Step 2.

$^1$H NMR δ (ppm)(CD$_3$OD): 7.81 (2H, d, J=8.2 Hz), 7.64 (2H, d, J=8.0 Hz), 7.19 (2H, t, J=7.9 Hz), 7.00-6.94 (1H, m), 3.82-3.70 (2H, m), 3.57 (1H, s), 3.35 (2H,s), 280-240 (4H, m), 2.21-2.13 (2H, m), 2.01 (2H, s), 1.88 (1H, d, J=14.6 Hz), 1.63-1.53 (3H, m).

The invention claimed is:
1. A compound according to one of the following formulae:

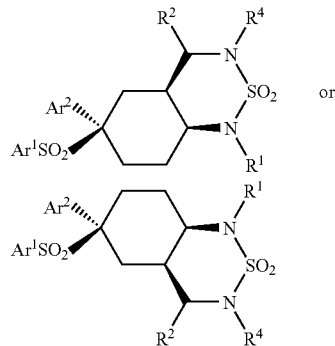

wherein
R$^1$ represents H or C$_{1-4}$alkyl;
R$^2$ and R$^4$ independently represent H or a hydrocarbon group of up to 10 carbon atoms, optionally substituted with CF$_3$, CHF$_2$, halogen, CN, OR$^5$, COR$^5$, CO$_2$R$^5$, OCOR$^6$, N(R$^5$)$_2$, CON(R$^5$)$_2$ or NR$^5$COR$^6$;
R$^5$ represents H or C$_{1-4}$alkyl;
R$^6$ represents C$_{1-4}$alkyl; and
Ar$^1$ and Ar$^2$ independently represent phenyl or heteroaryl, either of which bears 0-3 substituents independently selected from halogen, CN, NO$_2$, CF$_3$, CHF$_2$, OH, OCF$_3$, CHO, CH=NOH, C$_{1-4}$alkoxy, C$_{1-4}$alkoxycarbonyl, C$_{2-6}$acyl, C$_{2-6}$alkenyl and C$_{1-4}$alkyl which optionally bears a substituent selected from halogen, CN, NO$_2$, CF$_3$, OH and C$_{1-4}$alkoxy;
or a pharmaceutically acceptable salt thereof.

2. A compound according to claim 1
wherein $R^1$ represents H;
or a pharmaceutically acceptable salt thereof.

3. A compound according to claim 1 wherein $Ar^1$ is selected from 6-(trifluoromethyl)-3-pyridyl and phenyl which is optionally substituted in the 4-position with halogen, CN, vinyl, allyl, acetyl, methyl or mono-, di- or trifluoromethyl;
and $Ar^2$ represents 2,5-difluorophenyl, 2,6-difluorophenyl or 2,3,6-trifluorophenyl.

4. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,410,964 B2
APPLICATION NO. : 10/555034
DATED : August 12, 2008
INVENTOR(S) : Kevin Dinnell et al.

It is certified that error appears in the above-identified patent and that said Letters Patent is hereby corrected as shown below:

At column 21, line 15, the chemical structure should be deleted and replaced with:

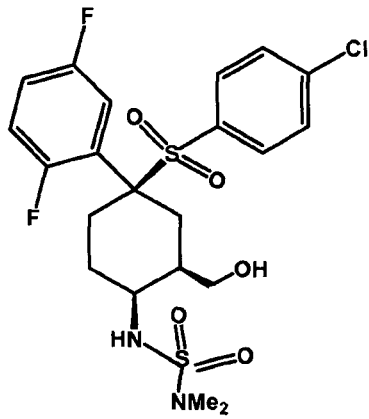

At column 22, line 42, "step 4" should read "step 5".

At column 35, line 15, the chemical structure should be deleted and replaced with:

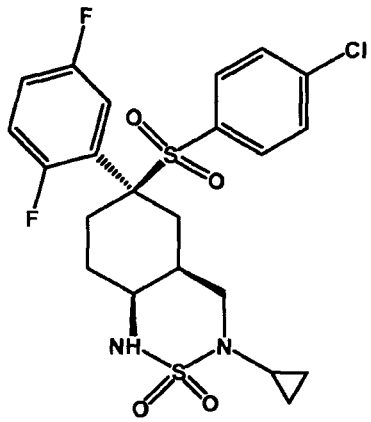

Signed and Sealed this
Sixteenth Day of August, 2011

David J. Kappos
*Director of the United States Patent and Trademark Office*